US008729097B2

(12) United States Patent
Liu et al.

(10) Patent No.: US 8,729,097 B2
(45) Date of Patent: May 20, 2014

(54) QUINOLINE COMPOUNDS AS INHIBITORS OF ANGIOGENESIS, HUMAN METHIONINE AMINOPEPTIDASE, AND SIRT1, AND METHODS OF TREATING DISORDERS

(75) Inventors: Jun O. Liu, Clarksville, MD (US); Joong Sup Shim, Owings Mills, MD (US); Curtis R. Chong, Honolulu, HI (US); Shridhar Bhat, Cockeysville, MD (US)

(73) Assignee: The Johns Hopkins University, Baltimore, MD (US)

( * ) Notice: Subject to any disclaimer, the term of this patent is extended or adjusted under 35 U.S.C. 154(b) by 321 days.

(21) Appl. No.: 13/122,876

(22) PCT Filed: Oct. 6, 2009

(86) PCT No.: PCT/US2009/005475
§ 371 (c)(1),
(2), (4) Date: Aug. 29, 2011

(87) PCT Pub. No.: WO2010/042163
PCT Pub. Date: Apr. 15, 2010

(65) Prior Publication Data
US 2011/0301163 A1       Dec. 8, 2011

Related U.S. Application Data

(60) Provisional application No. 61/102,919, filed on Oct. 6, 2008.

(51) Int. Cl.
*A61K 31/04* (2006.01)

(52) U.S. Cl.
USPC .......................................... 514/312

(58) Field of Classification Search
USPC ......................................... 546/159; 514/312
See application file for complete search history.

(56) References Cited

U.S. PATENT DOCUMENTS

| 4,758,264 | A | 7/1988 | Hubele |
| 5,380,852 | A | 1/1995 | Schütze et al. |
| 6,476,014 | B1 * | 11/2002 | Jordan et al. ............ 514/187 |
| 2006/0069161 | A1 * | 3/2006 | Lee et al. ............... 514/570 |
| 2006/0073182 | A1 * | 4/2006 | Wong et al. ............. 424/426 |
| 2006/0104968 | A1 * | 5/2006 | Bookbinder et al. ..... 424/94.61 |
| 2006/0167044 | A1 * | 7/2006 | Arnaiz et al. ........... 514/310 |

FOREIGN PATENT DOCUMENTS

| EP | 0254866 A1 | 2/1988 |
| JP | 05-097674 | 4/1993 |
| JP | 5097674 A | 4/1993 |
| WO | 9619458 A2 | 6/1996 |
| WO | 0116108 A2 | 3/2001 |
| WO | 0200625 A2 | 1/2002 |
| WO | 2004103998 A1 | 12/2004 |
| WO | 2005070006 * | 8/2005 |
| WO | 2006117660 * | 11/2006 |
| WO | WO-2006/117660 A2 | 11/2006 |
| WO | WO-2007/086663 A1 | 8/2007 |
| WO | WO-2008/013966 A2 | 1/2008 |
| WO | WO-2009/146546 A1 | 12/2009 |
| WO | 2007/048097 * | 4/2013 |

OTHER PUBLICATIONS

Podeszwa, Bioorg & MEd CHem Lett, VOl 17, pp. 6138-6141, 2007.*
Shen, J Pharm Pharmacol, vol. 51, pp. 543-548, 1999.*
Shim, J National cancer Institute, vol. 102(24), Dec. 15, 2010, pp. 1-19.*
Bhat S, et al. "Substituted oxines inhibit endothelial cell proliferation and angiogenesis." Org Biomol Chem. Apr. 21, 2012;10(15):2979-92.
Ding Wq, et al. "Anticancer activity of the antibiotic clioquinol." Cancer Res. Apr. 15, 2005;65(8):3389-95.
Musiol R, et al. "Investigating biological activity spectrum for novel quinoline analogues." Bioorg Med Chem. Feb. 1, 2007;15(3):1280-8.
Ungureanu M, et al. "Synthesis of New Antibacterian and Antifungal Derivatives of 8-Hydroxyquinoline" Analele Stintifice Ale Universitatii AL. I. Cuza Din Iasi, Sectiunea 1C: Chimie, Universitatea AI. I. Cuza: Cartimex, IASI, RO, vol. 7, noi. 1, Jan. 1, 1999: 55-60.
Supplementary European Search Report Issued Sep. 13, 2012 for European Patent Application No. EP09819542.
Chinese Office Action dated Nov. 11, 2013 in corresponding Chinese Patent Application No. 200980148990.0 (with English Translation or Summary).

* cited by examiner

*Primary Examiner* — D M Seaman
(74) *Attorney, Agent, or Firm* — Edwards Wildman Palmer LLP; Peter F. Corless

(57) ABSTRACT

Described herein are methods of inhibiting methionine aminopeptidase or SirT1, inhibiting angiogenesis, and treating disorders (or symptoms thereof) associated with methionine aminopeptidase, SirT1 and/or angiogenesis, wherein a compound of the invention is administered to a subject.

22 Claims, 15 Drawing Sheets

FIG. 1

Table 1. Effects of nitroxoline on MetAP enzyme activity and cell proliferation.

| MetAP activity | | | | Cell proliferation | | | |
|---|---|---|---|---|---|---|---|
| Drug | Isotype | Metal ion | IC$_{50}$ (µM) | Drug | Cell line | IC$_{50}$ (µM) | Action |
| Nitroxoline | MetAP-1 | Co$^{2+}$ | >50 | Nitroxoline | HUVECs | 1.98 | Cytostatic |
| | | Mn$^{2+}$ | >50 | | HCC1599 | 2.85 | Cytostatic |
| | MetAP-2 | Co$^{2+}$ | 11.20 | | HCC1937 | 4.50 | Cytostatic |
| | | Mn$^{2+}$ | 0.46 | | HCC1954 | 2.96 | Cytostatic |
| | | | | | HCC2218 | 4.23 | Cytostatic |
| | | | | | MCF-10A | 2.15 | Cytostatic |
| IV-43 | MetAP-1 | Co$^{2+}$ | 1.50 | IV-43 | HUVECs | 0.65 | Cytostatic |
| | | Mn$^{2+}$ | >50 | | | | |
| TNP-470 | MetAP-2 | Co$^{2+}$ | 0.002 | TNP-470 | HUVECs | 8.5x10$^{-4}$ | Cytostatic |
| | | Mn$^{2+}$ | 0.002 | | | | |

QUINOLINE COMPOUNDS AS INHIBITORS OF ANGIOGENESIS, HUMAN METHIONINE AMINOPEPTIDASE, AND SIRT1, AND METHODS OF TREATING DISORDERS

RELATED APPLICATIONS

This application is a 35 U.S.C. §371 U.S. national entry of International Application PCT/US2009/005475 (WO 2010/042163) having an International filing date of Oct. 6, 2009 which claims the benefit of U.S. Provisional Application Ser. No. 61/102,919, filed Oct. 6, 2008. The entire contents of the provisional application are incorporated herein by this reference.

BACKGROUND OF THE INVENTION

Protein synthesis is initiated with a methionine residue in eukaryotic cells, or a formylated methionine in prokaryotes, mitochondria and chloroplasts. For a large subset of proteins, the initiator methionine is cotranslationally removed prior to further post-translational modification. The proteolytic removal of N-terminal methionine is catalyzed by a family of enzymes known as methionine aminopeptidases (MetAPs). The functions of these enzymes are evolutionarily conserved and essential, as demonstrated by the lethal phenotype of the map null mutant in bacteria. Although only one MetAP gene is present in the genome of most, but not all, prokaryotes, at least two types of MetAPs, type I and type II, are known in eukaryotic cells. In budding yeast *Saccharomyces cerevisiae*, deletion of either ScMetAP1 or ScMetAP2 resulted in a slow-growth phenotype compared to the wild type strain, whereas the double mutant is non-viable, indicating the redundant yet essential functions of both types of MetAP (Chang, Y. H., et al. (1992) *J. Biol. Chem.* 267, 8007-8011; Li, X. & Chang, Y. H. (1995) *Proc. Natl. Acad. Sci. U. S. A.* 92, 12357-12361). In multi-cellular organisms, MetAP2 has been shown to be essential for the proliferation and development of specific tissues (Boxem, M., et al., (2004) *FEBS Lett.* 576, 245-250; Cutforth, T. & Gaul, U. (1999) *Mech. Dev.* 82, 23-28).

Human MetAP2 has been identified as the primary target of the fumagillin family of natural products that potently inhibit angiogenesis (Griffith, E. C., et al. (1997) *Chem. Biol.* 4, 461-471; Sin, N., et al. (1997) *Proc. Natl. Acad. Sci. U. S. A.* 94, 6099-6103). A synthetic analog of fumagillin, TNP-470 with higher potency and lower toxicity, has entered clinical trials for a variety of cancers (Ingber, D., et al. (1990) *Nature* 348, 555-557; Satchi-Fainaro, R., et al. (2005) *Cancer Cell* 7, 251-261). Much evidence now exists supporting the notion that HsMetAP2 plays an important role in endothelial cell proliferation and is likely to mediate inhibition of endothelial cells by fumagillin and related analogs (Griffith, E. C., et al. (1997) *Chem. Biol.* 4, 461-471; Sin, N., et al. (1997) *Proc. Natl. Acad. Sci. U. S. A.* 94, 6099-6103; Yeh, J. R., et al. (2006) *Proc. Natl. Acad. Sci. U. S. A.* 103, 10379-10384).

Angiogenesis may be defined as the development of a blood supply to a given area of tissue. The development of a blood supply may be part of normal embryonic development, represent the revascularization of a wound bed, or involve the stimulation of vessel growth by inflammatory or malignant cells. Sometimes angiogenesis is defined as the proliferation of new capillaries from pre-existing blood vessels. New growth of soft tissue requires new vascularization, and the concept of angiogenesis is a key component of tissue growth and in particular, a key point of intervention in pathological tissue growth.

Angiogenesis is a fundamental process necessary for embryonic development, subsequent growth, and tissue repair. Angiogenesis is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g., in the healing of wounds and fractures.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating new blood vessels. Creation of the new microvascular system can initiate or exacerbate disease conditions.

Medical science has recognized that angiogenesis is an important factor in the initiation and/or proliferation of a large number of diverse disease conditions. Under normal physiological conditions, humans and other animals only undergo angiogenesis in very specific, restricted situations. For example, angiogenesis is normally observed in wound healing, fetal and embryonic development, and in the formation of the corpus luteum, endometrium and placenta. The process of angiogenesis has been found to be altered in a number of disease states, and in many instances, the pathological damage associated with the disease is related to uncontrolled angiogenesis. Since it was first put forward over thirty years ago, the hypothesis that angiogenesis is required for tumor growth and metastasis has gained extensive experimental support (Folkman, J. (1971) *N. Engl. J. Med.* 285, 1182-1186, Hanahan, D. & Folkman, J. (1996) *Cell* 86, 353-364). For example, angiogenesis is a factor in tumor growth, since a tumor must continuously stimulate growth of new capillary blood vessels in order to grow. Angiogenesis is an essential part of the growth of human solid cancer, and abnormal angiogenesis is associated with other diseases such as rheumatoid arthritis, psoriasis, and diabetic retinopathy (Folkman, J. and Klagsbrun, M., Science 235:442-447, (1987)). In addition to tumor growth and metastasis, angiogenesis has also been implicated in rheumatoid arthritis, diabetic retinopathy and macular degeneration, suggesting that inhibition of angiogenesis may be useful for the treatment of these disorders (Carmeliet, P. (2003) *Nat. Med.* 9, 653-660).

Angiogenesis, the formation of new blood vessels, has been implicated in the pathogenesis of several important human diseases, including cancer, diabetic retinopathy, and age-related macular degeneration. Inhibition of angiogenesis is emerging as an effective new strategy for the treatment of angiogenesis-dependent diseases. One of the most potent classes of small molecule inhibitors is from the fumagillin family. Fumagillin, its synthetic analogue TNP-470, and ovalicin have been shown to specifically bind to type 2 methionine aminopeptidase (MetAP2). In a mechanism that remains to be completely elucidated, inhibition of MetAP2 by these small molecule inhibitors led to the transcriptional activation of p53, which in turn activates the expression of p21 that inhibits cyclinE•Cdk2, accounting for the cell cycle blockade by these inhibitors. Since the identification of MetAP2 as the target for fumagillin and ovalicin, a number of attempts have been made to find new and reversible inhibitors of this enzyme through either the structural modification of fumagillin or high-throughput screening.

Clearly, the development and progress of many disease conditions can be controlled by controlling the process of angiogenesis, and in particular, through the inhibition of MetAP. There is a need for methods and materials capable of controlling and inhibiting angiogenesis in a reliable manner. It is therefore an object of the invention to provide compounds and pharmaceutical compositions which exhibit activity as inhibitors of angiogenesis.

SUMMARY OF THE INVENTION

In one aspect, the invention provides a compound of formula I:

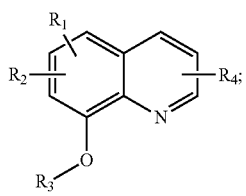

(I)

or a pharmaceutically acceptable salt thereof,
wherein,
$R_1$ is H, nitro, halo, an optionally substituted alkyl, an optionally substituted alkenyl, an optionally substituted aryl, an optionally substituted heteroaryl, optionally substituted heterocycloalkyl, $NR_A R_A$, or $SO_3 R_A$;
$R_2$ is H, nitro, halo, an optionally substituted alkyl, an optionally substituted alkenyl, an optionally substituted aryl, an optionally substituted heteroaryl, optionally substituted heterocycloalkyl, $NR_A R_A$, $SO_3 R_A$, or $SR_A$;
$R_4$ is H, nitro, halo, an optionally substituted alkyl, an optionally substituted alkenyl, an optionally substituted aryl, an optionally substituted heteroaryl, optionally substituted heterocycloalkyl, $NR_A R_A$, or $SO_3 R_A$;
$R_3$ is H, $C(O)R_B$, $C(O)OR_B$, $C(O)NHR_B$, an optionally substituted alkyl, an optionally substituted alkenyl, an optionally substituted aryl, an optionally substituted aralkyl, an optionally substituted heteroaryl, or optionally substituted heterocycloalkyl;
each $R_A$ is independently H or an optionally substituted alkyl; and
each $R_B$ is independently H, an optionally substituted alkyl, or an optionally substituted aryl.

In a second aspect, the invention provides a method of treating a disease or disorder associated with methionine aminopeptidase or SirT1 in a subject, the method comprising the step of administering to the subject an effective amount of a compound of formula I, or a compound of any of the formulae provided herein.

In another aspect, the invention provides a method of treating a disease or disorder associated with methionine aminopeptidase in a subject, wherein the subject is identified as being in need of a type 2 methionine aminopeptidase inhibitor, the method comprising the step of administering to the subject an effective amount of a compound of formula I, or a compound of any of the formulae provided herein.

In still another aspect, the invention provides a method of treating a disease or disorder associated with SirT1 in a subject, wherein the subject is identified as being in need of a SirT1 inhibitor, the method comprising the step of administering to the subject an effective amount of a compound of formula I, or a compound of any of the formulae provided herein.

In other aspects, the invention provides a method of treating a disease or disorder associated with angiogenesis in a subject, the method comprising the step of administering to the subject an effective amount of a compound of formula I, or a compound of any of the formulae provided herein.

In another aspect, the invention provides a method of inhibiting or reducing methionine aminopeptidase or SirT1 in a subject, the method comprising the step of administering to the subject an effective amount of a compound of formula I, or a compound of any of the formulae provided herein; wherein said compound is identified in a screening assay.

In other aspects, the invention provides a method of inhibiting or reducing angiogenesis in a subject, the method comprising the step of administering to the subject an effective amount of a compound of formula I, or a compound of any of the formulae provided herein.

In still other aspects, the invention provides a method of treating tumor, cancer growth, or neoplasia in a subject, the method comprising the step of administering to the subject an effective amount of a compound of formula I, or a compound of any of the formulae provided herein.

In other aspects, the invention provides the use of a compound in the manufacture of a medicament for inhibiting type 2 methionine aminopeptidase in a patient, wherein the compound is a compound of formula I, or a compound of any of the formulae provided herein.

In another aspect, the invention provides the use of a compound in the manufacture of a medicament for inhibiting SirT1 in a patient, wherein the compound is a compound of formula I, or a compound of any of the formulae provided herein.

In certain aspects, the invention provides the use of a compound in the manufacture of a medicament for inhibiting angiogenesis in a patient, wherein the compound is a compound of formula I, or a compound of any of the formulae provided herein.

In certain aspects, the invention also provides for a pharmaceutical composition comprising a compound of formula I, or a compound of any of the formulae provided herein, and a pharmaceutically suitable excipient.

In other aspects, the invention provides a kit comprising an effective amount of a compound of formula I, or a compound of any of the formulae provided herein, in unit dosage form, together with instructions for administering the compound to a subject suffering from or susceptible to a methionine aminopeptidase-related, SirT1-related, or angiogenesis-related disease.

BRIEF DESCRIPTION OF THE DRAWINGS

FIG. 1. Effects of nitroxoline on MetAP enzyme activities and cell proliferation.

DETAILED DESCRIPTION OF THE INVENTION

I. Definitions

Figure 2A:
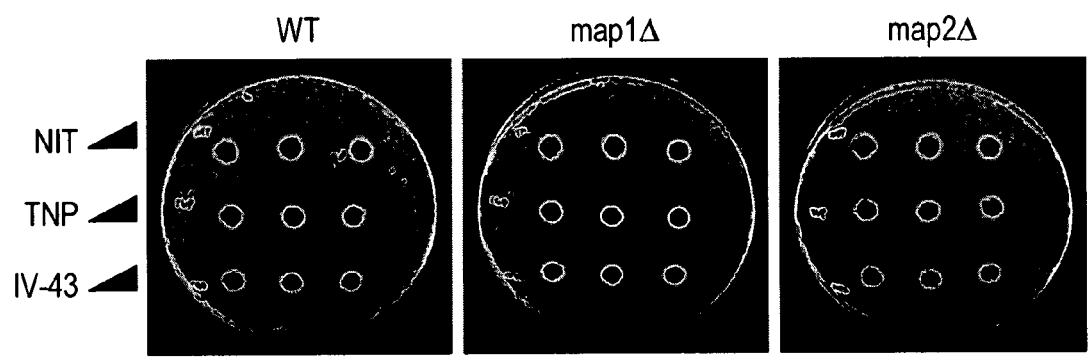
FIG. 2. Effects of nitroxoline on in vivo function of MetAP-2. A, Selective inhibition of MetAP-2 function by nitroxoline in yeasts. Wild type (WT) and mutant yeasts were treated with nitroxoline or IV-43 at the concentrations of 0, 0.2, and 2 nmol in each paper disc for 24 h. TNP-470 was treated in the concentrations of 0, 0.1, 1 nmol for 24 h. B, Inhibition of N-terminal methionine processing of 14-3-3γ in HUVEC by nitroxoline, MetAP2-siRNA, or TNP-470. HUVEC were treated with either nitroxoline or TNP-470 for 24 h and N-terminal methionylated 14-3-3γ was detected using a specific antibody. For MetAP2 knock down experiment, HUVEC were transfected with different concentrations of MetAP2-siRNA for 48 h and harvested for western blot.

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of alkyl radicals include, but are not limited to, methyl, ethyl, propyl, isopropyl, n-butyl, tert-butyl, neopentyl, n-hexyl heptyl, octyl radicals.

The term "alkenyl," as used herein, denote a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denote a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "cycloalkyl" or "carbocyclic" are used interchangeably, and as used herein, denotes a monovalent group derived from a monocyclic or polycyclic saturated carbocyclic ring compound. Examples include, but are not limited to, cyclopropyl, cyclobutyl, cyclopentyl, cyclohexyl, cyclopentyl and cyclooctyl; bicyclo [2.2.1] heptyl, and bicyclo [2.2.2] octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "aryl," as used herein, refers to a mono- or polycyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy,

—$NO_2$, —CN,

—$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloallcyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$- heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalleyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalleyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalleyl, —S-aryl, —S-heteroaryl, —S-heterocycloalkyl, or methylthiomethyl.

It is understood that the aryls, heteroaryls, alkyls, and the like can be further substituted. In accordance with the invention, any of the aryls, substituted aryls, heteroaryls and substituted heteroaryls described herein, can be any aromatic group. Aromatic groups can be substituted or unsubstituted.

The terms "hal," "halo" and "halogen," are used interchangeably, and as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "effective amount" is used throughout the specification to describe concentrations or amounts of compounds according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated.

As used herein, the terms "prevent," "preventing," "prevention," and the like refer to reducing the probability of developing a disorder or condition in a subject, who does not have, but is at risk of or susceptible to developing a disorder or condition.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "anti-angiogenic compound" and "angiogenesis inhibiting compound" may be used interchangeably. Angiogenesis is used throughout the specification to describe the biological processes which result in the development of blood vessels or increase in the vascularity of tissue in an organism. Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

The term "tumor" is used to describe an abnormal growth in tissue which occurs when cellular proliferation is more rapid than normal tissue and continues to grow after the stimuli that initated the new growth cease. Tumors generally exhibit partial or complete lack of structural organization and functional coordination with the normal tissue, and usually form a distinct mass of tissue which may be benign (benign tumor) or malignant (carcinoma). Tumors tend to be highly vascularized.

The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor. Methods of treating tumors and/or cancer according to the present invention comprise administering to a patient in need thereof an effective amount of one or compounds according to the present invention.

II. Compounds of the Invention

In one aspect, the invention provides a compound of formula I:

$$\text{(I)}$$

or a pharmaceutically acceptable salt thereof,
wherein, $R_1$ is H, nitro, halo, an optionally substituted alkyl, an optionally substituted alkenyl, an optionally substituted aryl, an optionally substituted heteroaryl, optionally substituted heterocycloalkyl, $NR_AR_A$, or $SO_3R_A$;

$R_2$ is H, nitro, halo, an optionally substituted alkyl, an optionally substituted alkenyl, an optionally substituted aryl, an optionally substituted heteroaryl, optionally substituted heterocycloalkyl, $NR_AR_A$, $SO_3R_A$, or $SR_A$;

$R_4$ is H, nitro, halo, an optionally substituted alkyl, an optionally substituted alkenyl, an optionally substituted aryl, an optionally substituted heteroaryl, optionally substituted heterocycloalkyl, $NR_AR_A$, or $SO_3R_A$;

$R_3$ is H, $C(O)R_B$, $C(O)OR_B$, $C(O)NHR_B$, an optionally substituted alkyl, an optionally substituted alkenyl, an optionally substituted aryl, an optionally substituted aralkyl, an optionally substituted heteroaryl, or optionally substituted heterocycloalkyl;

each $R_A$ is independently H or an optionally substituted alkyl; and each $R_B$ is independently H, an optionally substituted alkyl, or an optionally substituted aryl.

In a first embodiment, the invention provides a compound of formula II:

$$\text{(II)}$$

or a pharmaceutically acceptable salt thereof,
wherein, $R_1$ is H, nitro, halo, an optionally substituted alkyl, an optionally substituted alkenyl, an optionally substituted aryl, an optionally substituted heteroaryl, optionally substituted heterocycloalkyl, $NR_AR_A$, or $SO_3R_A$;

$R_2$ is H, nitro, halo, an optionally substituted alkyl, an optionally substituted alkenyl, an optionally substituted aryl, an optionally substituted heteroaryl, optionally substituted heterocycloalkyl, $NR_AR_A$, $SO_3R_A$, or $SR_A$;

each $R_A$ is independently H or an optionally substituted alkyl; and each $R_B$ is independently H, an optionally substituted alkyl, or an optionally substituted aryl.

In certain embodiments, $R_1$ is H, nitro, Cl, Br, or $SO_3H$.

In other embodiments, $R_2$ is H or an optionally substituted alkyl.

In a further embodiment, $R_2$ is methyl which is optionally substituted by one or more of phenyl, naphthyl, anthracenyl, fluorenyl, indenyl, azulenyl; pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, indazolyl, imidazopyridyl, quinazolinyl, purinyl, pyrrolo[2,3]pyrimidinyl, pyrazolo[3,4]pyrimidinyl, benzo(b)thienyl; cyclopropyl, cyclobutyl, cyclopentyl, cyclohexyl, cycloheptyl, aziridinyl, oxiranyl, azetidinyl, oxetanyl; piperidinyl, piperazinyl, 2-oxopiperazinyl, 2-oxopiperidinyl, 2-oxo pyrrolidinyl, 4-piperidonyl, tetrahydropyranyl, oxazolidinyl, 2-oxo-oxazolidinyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydropyranyl, or tetrahydrothienyl; each of which may be optionally substituted. In a further embodiment, $R_2$ is methyl which is optionally substituted by one or more of alkyl, alkenyl, hydroxy, or $NR_AR_A$.

In a second embodiment, the invention provides a compound of formula III:

$$\text{(III)}$$

or a pharmaceutically acceptable salt thereof,
wherein, $R_1$ is H, nitro, halo, an optionally substituted alkyl, an optionally substituted alkenyl, an optionally substituted aryl, an optionally substituted heteroaryl, optionally substituted heterocycloalkyl, $NR_AR_A$, or $SO_3R_A$;

$R_2$ is H, nitro, halo, an optionally substituted alkyl, an optionally substituted alkenyl, an optionally substituted aryl, an optionally substituted heteroaryl, optionally substituted heterocycloalkyl, $NR_AR_A$, $SO_3R_A$, or $SR_A$;

$R_3$ is $C(O)R_B$, $C(O)OR_B$, $C(O)NHR_B$, an optionally substituted alkyl, or an optionally substituted alkenyl;

each $R_A$ is independently H or an optionally substituted alkyl; and each $R_B$ is independently H, an optionally substituted alkyl, or an optionally substituted aryl.

In certain embodiments, $R_1$ is H, nitro, Cl, Br, an optionally substituted alkyl, an optionally substituted alkenyl, an optionally substituted aryl, an optionally substituted heteroaryl, optionally substituted heterocycloalkyl, $NR_4R_4$, or $SO_3R_4$.

In a further embodiment, $R_1$ is an optionally substituted alkyl, an optionally substituted aryl, an optionally substituted heteroaryl, or optionally substituted heterocycloalkyl. In a further embodiment, $R_1$ is optionally substituted by one or more of phenyl, naphthyl, anthracenyl, fluorenyl, indenyl, azulenyl; pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, indazolyl, imidazopyridyl, quinazolinyl, purinyl, pyrrolo[2,3]pyrimidinyl, pyrazolo[3,4]pyrimidinyl, benzo(b)thienyl; cyclopropyl, cyclobutyl, cyclopentyl, cyclohexyl, cycloheptyl, aziridinyl, oxiranyl, azetidinyl, oxetanyl; piperidinyl, piperazinyl, 2-oxopiperazinyl, 2-oxopiperidinyl, 2-oxo pyrrolidinyl, 4-piperidonyl, tetrahydropyranyl, oxazolidinyl, 2-oxo-oxazolidinyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, or tetrahydrothienyl; each of which may be optionally substituted.

In other embodiments, $R_2$ is H, nitro, Cl, or Br.

In still other embodiments, $R_3$ is $C(O)R_B$, $C(O)OR_B$, $C(O)NHR_B$, an optionally substituted alkyl or an optionally substituted alkenyl. In a further embodiment, $R_3$ is an optionally substituted ethyl, allyl, or $C(O)NHR_B$, wherein $R_B$ is an optionally substituted phenyl or optionally substituted alkyl.

In a third embodiment, the invention provides a compound of formula IV:

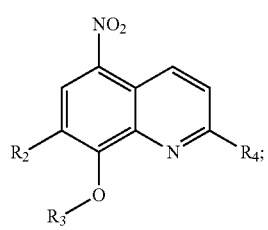

(IV)

or a pharmaceutically acceptable salt thereof,
wherein,
$R_2$ is H, nitro, halo, an optionally substituted alkyl, an optionally substituted alkenyl, an optionally substituted aryl, an optionally substituted heteroaryl, optionally substituted heterocycloalkyl, $NR_4R_4$, or $SO_3R_4$;

$R_4$ is H, nitro, halo, an optionally substituted alkyl, an optionally substituted alkenyl, an optionally substituted aryl, an optionally substituted heteroaryl, optionally substituted heterocycloalkyl, $NR_4R_4$, or $SO_3R_4$;

$R_3$ is H, $C(O)R_B$, $C(O)OR_B$, $C(O)NHR_B$, an optionally substituted alkyl, or an optionally substituted alkenyl;

each $R_A$ is independently H, or an optionally substituted alkyl; and each $R_B$ is independently H, an optionally substituted alkyl, or an optionally substituted aryl.

In certain embodiments, $R_2$ is H or nitro.

In another embodiment, $R_4$ is H or an optionally substituted alkyl.

In still other embodiments, $R_3$ is H, $C(O)R_B$, $C(O)OR_B$, or an optionally substituted alkyl.

Certain compounds of the present invention may exist in particular geometric, isomeric, or stereoisomeric forms. The present invention contemplates all such compounds, including cis- and trans-isomers, R- and S-enantiomers, racemates and racemic mixtures, single enantiomers, individual diastereomers, diastereomeric mixtures diastereomers, (D)-isomers, (L)-isomers, the racemic mixtures thereof, and other mixtures thereof, as falling within the scope of the invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). Additional asymmetric carbon atoms may be present in a substituent such as an alkyl group. All such enriched isomers, as well as racemic mixtures thereof, are intended to be included in this invention. All such isomeric forms of such compounds are expressly included in the present invention. All crystal forms of the compounds described herein are expressly included in the present invention.

The compounds described above can be prepared by methods well known in the art, as well as by the synthetic routes disclosed in the examples below.

The chemicals used in the above-described synthetic route may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the heterocyclic compounds. In addition, various synthetic steps may be performed in an alternate sequence or order to give the desired compounds. Synthetic chemistry transformations and protecting group methodologies (protection and deprotection) useful in synthesizing applicable heterocyclic compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Correspondingly, the compounds described herein can be made according to methods know in the art, including those in the aforementioned treatises. It is recognized by one of ordinary skill that reaction conditions (e.g., temperature, reaction time, etc.) may be adjusted, which is routine for one of ordinary skill.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2nd. Ed., Wiley-VCH Publishers (1999); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

III. Methods of Treatment

In certain aspects, the invention provides a method of treating a disease or disorder associated with methionine aminopeptidase or SirT1 in a subject, the method comprising the step of administering to the subject an effective amount of a compound of formula I:

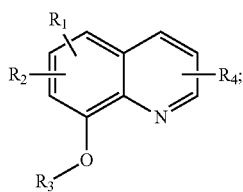

(I)

or a pharmaceutically acceptable salt thereof, wherein, $R_1$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_2$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_4$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_3$ is H, $C(O)R_B$, $C(O)OR_B$, $C(O)NHR_B$, $C(O)NR_BR_B$, an optionally substituted alkyl, an optionally substituted alkenyl, an optionally substituted alkynyl, an optionally substituted aryl, an optionally substituted aralkyl, an optionally substituted heteroaryl, or optionally substituted heterocycloalkyl;

each $R_A$ is independently H, an optionally substituted alkyl, an optionally substituted aryl, an optionally substituted aralkyl, an optionally substituted heteroaryl, or optionally substituted heterocyclic; and each $R_B$ is independently H, an optionally substituted alkyl, an optionally substituted aryl, an optionally substituted aralkyl, an optionally substituted heteroaryl, or optionally substituted heterocyclic.

In another aspect, the invention provides a method of treating a disease or disorder associated with methionine aminopeptidase in a subject, wherein the subject is identified as being in need of a type 2 methionine aminopeptidase inhibitor, the method comprising the step of administering to the subject an effective amount of a compound of formula I:

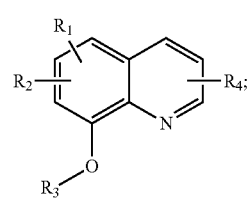

(I)

or a pharmaceutically acceptable salt thereof, wherein, $R_1$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_2$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_4$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_3$ is H, $C(O)R_B$, $C(O)OR_B$, $C(O)NHR_B$, $C(O)NR_BR_B$, an optionally substituted alkyl, an optionally substituted alkenyl, an optionally substituted alkynyl, an optionally substituted aryl, an optionally substituted aralkyl, an optionally substituted heteroaryl, or optionally substituted heterocycloalkyl;

each $R_A$ is independently H, an optionally substituted alkyl, an optionally substituted aryl, an optionally substituted aralkyl, an optionally substituted heteroaryl, or optionally substituted heterocyclic; and each $R_B$ is independently H, an optionally substituted alkyl, an optionally substituted aryl, an optionally substituted aralkyl, an optionally substituted heteroaryl, or optionally substituted heterocyclic.

In still another aspect, the invention provides a method of treating a disease or disorder associated with SirT1 in a subject, wherein the subject is identified as being in need of a SirT1 inhibitor, the method comprising the step of administering to the subject an effective amount of a compound of formula I:

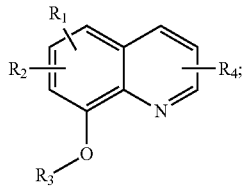

(I)

or a pharmaceutically acceptable salt thereof,
wherein, $R_1$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_2$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_4$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_3$ is H, $C(O)R_B$, $C(O)OR_B$, $C(O)NHR_B$, $C(O)NR_BR_B$, an optionally substituted alkyl, an optionally substituted alkenyl, an optionally substituted alkynyl, an optionally substituted aryl, an optionally substituted aralkyl, an optionally substituted heteroaryl, or optionally substituted heterocycloalkyl;

each $R_A$ is independently H, an optionally substituted alkyl, an optionally substituted aryl, an optionally substituted aralkyl, an optionally substituted heteroaryl, or optionally substituted heterocyclic; and each $R_B$ is independently H, an optionally substituted alkyl, an optionally substituted aryl, an optionally substituted aralkyl, an optionally substituted heteroaryl, or optionally substituted heterocyclic.

In other aspects, the invention provides a method of treating a disease or disorder associated with angiogenesis in a subject, the method comprising the step of administering to the subject an effective amount of a compound of formula I:

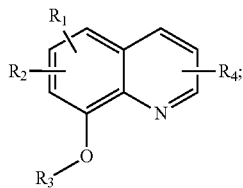

(I)

or a pharmaceutically acceptable salt thereof,
wherein, $R_1$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_2$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_4$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_3$ is H, $C(O)R_B$, $C(O)OR_B$, $C(O)NHR_B$, $C(O)NR_BR_B$, an optionally substituted alkyl, an optionally substituted alkenyl, an optionally substituted alkynyl, an optionally substituted aryl, an optionally substituted aralkyl, an optionally substituted heteroaryl, or optionally substituted heterocycloalkyl;

each $R_A$ is independently H, an optionally substituted alkyl, an optionally substituted aryl, an optionally substituted aralkyl, an optionally substituted heteroaryl, or optionally substituted heterocyclic; and each $R_B$ is independently H, an optionally substituted alkyl, an optionally substituted aryl, an optionally substituted aralkyl, an optionally substituted heteroaryl, or optionally substituted heterocyclic.

In certain embodiments, the disease or disorder associated with methionine aminopeptidase, SirT1, or angiogenesis is selected from: tumor or cancer growth (neoplasia), skin disorders, neovascularization, inflammatory and arthritic diseases, retinoblastoma, cystoid macular edema (CME), exudative age-related macular degeneration (AMD), diabetic retinopathy, diabetic macular edema, or ocular inflammatory disorders.

In certain embodiments, the disease or disorder associated with angiogenesis is tumor or cancer growth (neoplasia). In a further embodiment, the disease or disorder is ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer, throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In other embodiments, the disease or disorder associated with angiogenesis is a skin disorder. In a further embodiment, the disease or disorder is psoriasis, acne, rosacea, warts, eczema, hemangiomas, lymphangiogenesis, Sturge-Weber syndrome, venous ulcers of the skin, neurofibromatosis, and tuberous sclerosis.

In certain embodiments, the disease or disorder associated with angiogenesis is neovascularization. In a further embodiment, the disease or disorder is diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications, and diseases associated with rubeosis (neovascularization of the ankle).

In certain embodiments, the disease or disorder associated with angiogenesis is inflammatory and arthritic disease. In a further embodiment, the disease or disorder is rheumatoid arthritis, osteoarthritis, lupus, scleroderma, Crohn's disease, ulcerative colitis, psoriasis, sarcoidosis, Sarcoidosis, skin lesions, hemangiomas, Osler-Weber-Rendu disease, hereditary hemorrhagic telangiectasia, and osteoarthritis.

In other embodiments, the disease or disorder affects the dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

In another aspect, the invention provides a method of inhibiting or reducing methionine aminopeptidase or SirT1 in a subject, the method comprising the step of administering to the subject an effective amount of a compound of formula I:

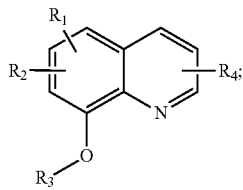

(I)

or a pharmaceutically acceptable salt thereof,
wherein,
$R_1$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;
$R_2$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;
$R_4$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_3$ is H, $C(O)R_B$, $C(O)OR_B$, $C(O)NHR_B$, $C(O)NR_BR_B$, an optionally substituted alkyl, an optionally substituted alkenyl, an optionally substituted alkynyl, an optionally substituted aryl, an optionally substituted aralkyl, an optionally substituted heteroaryl, or optionally substituted heterocycloalkyl;
each $R_A$ is independently H, an optionally substituted alkyl, an optionally substituted aryl, an optionally substituted aralkyl, an optionally substituted heteroaryl, or optionally substituted heterocyclic; and
each $R_B$ is independently H, an optionally substituted alkyl, an optionally substituted aryl, an optionally substituted aralkyl, an optionally substituted heteroaryl, or optionally substituted heterocyclic;
wherein said compound is identified in a screening assay.

In certain embodiments, the screening assay is selected from MetAP enzyme assay, Double Thymidine synchronization, Cell cycle analysis, and siRNA Transfection, $^3$H-thymidine incorporation assay, and sirtuin enzyme assay. In further embodiments, the screening assay is selected from MetAP enzyme assay, $^3$H-thymidine incorporation assay, and sirtuin enzyme assay.

In another embodiment, the inhibitor has a $IC_{50}$ for inhibiting type 2 methionine aminopeptidase less than about 5 micromolar.

In other aspects, the invention provides a method of inhibiting or reducing angiogenesis in a subject, the method comprising the step of administering to the subject an effective amount of a compound of formula I:

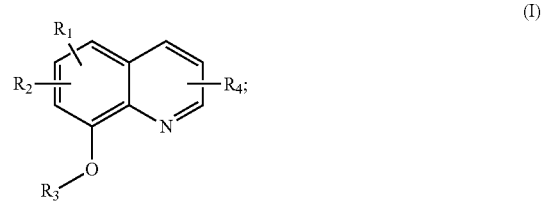

(I)

or a pharmaceutically acceptable salt thereof,
wherein,
$R_1$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;
$R_2$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;
$R_4$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;
$R_3$ is H, $C(O)R_B$, $C(O)OR_B$, $C(O)NHR_B$, $C(O)NR_BR_B$, an optionally substituted alkyl, an optionally substituted alkenyl, an optionally substituted alkynyl, an optionally substituted aryl, an optionally substituted aralkyl, an optionally substituted heteroaryl, or optionally substituted heterocycloalkyl;

each $R_A$ is independently H, an optionally substituted alkyl, an optionally substituted aryl, an optionally substituted aralkyl, an optionally substituted heteroaryl, or optionally substituted heterocyclic; and each $R_B$ is independently H, an optionally substituted alkyl, an optionally substituted aryl, an optionally substituted aralkyl, an optionally substituted heteroaryl, or optionally substituted heterocyclic.

In still other aspects, the invention provides a method of treating tumor, cancer growth, or neoplasia in a subject, the method comprising the step of administering to the subject an effective amount of a compound of formula I:

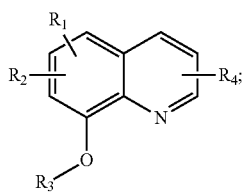
(I)

or a pharmaceutically acceptable salt thereof,
wherein, $R_1$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_2$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_4$ is H, hydroxy, cyano, nitro, azido, halo, an optionally substituted alkyl, an optionally substituted alkenyl, an optionally substituted alkynyl, an optionally substituted aryl, an optionally substituted aralkyl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_3$ is H, $C(O)R_B$, $C(O)OR_B$, $C(O)NHR_B$, $C(O)NR_BR_B$, an optionally substituted alkyl, an optionally substituted alkenyl, an optionally substituted alkynyl, an optionally substituted aryl, an optionally substituted aralkyl, an optionally substituted heteroaryl, or optionally substituted heterocycloalkyl;

each $R_A$ is independently H, an optionally substituted alkyl, an optionally substituted aryl, an optionally substituted aralkyl, an optionally substituted heteroaryl, or optionally substituted heterocyclic; and each $R_B$ is independently H, an optionally substituted alkyl, an optionally substituted aryl, an optionally substituted aralkyl, an optionally substituted heteroaryl, or optionally substituted heterocyclic.

In one embodiment, the compound inhibits type 2 methionine aminopeptidase to thereby treat the tumor, cancer growth, or neoplasia.

In another embodiment, the compound inhibits SirT1 to thereby treat the tumor, cancer growth, or neoplasia.

In certain embodiments, the compound is a compound of formula II:

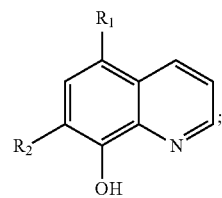
(II)

or a pharmaceutically acceptable salt thereof,
wherein, $R_1$ is H, nitro, halo, an optionally substituted alkyl, an optionally substituted alkenyl, an optionally substituted aryl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_2$ is H, nitro, halo, an optionally substituted alkyl, an optionally substituted alkenyl, an optionally substituted aryl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$; and each $R_A$ is independently H, an optionally substituted alkyl, an optionally substituted aryl, an optionally substituted aralkyl, an optionally substituted heteroaryl, or optionally substituted heterocyclic.

In other embodiments, the compound is a compound of formula III:

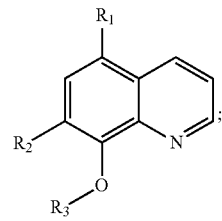
(III)

or a pharmaceutically acceptable salt thereof,
wherein, $R_1$ is H, nitro, halo, an optionally substituted alkyl, an optionally substituted alkenyl, an optionally substituted aryl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_2$ is H, nitro, halo, an optionally substituted alkyl, an optionally substituted alkenyl, an optionally substituted aryl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;

$R_3$ is $C(O)R_B$, $C(O)OR_8$, $C(O)NHR_B$, $C(O)NR_BR_B$, an optionally substituted alkyl, an optionally substituted alkenyl, an optionally substituted aryl, an optionally substituted aralkyl, an optionally substituted heteroaryl, or optionally substituted heterocycloalkyl;

each $R_A$ is independently H, an optionally substituted alkyl, an optionally substituted aryl, an optionally substituted aralkyl, an optionally substituted heteroaryl, or optionally substituted heterocyclic; and each $R_B$ is independently H, an optionally substituted alkyl, an optionally substituted aryl, an optionally substituted aralkyl, an optionally substituted heteroaryl, or optionally substituted heterocyclic.

In various embodiments, the compound is a compound of formula IV:

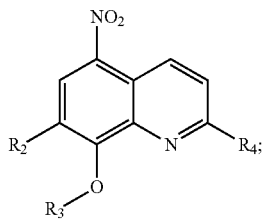

(IV)

or a pharmaceutically acceptable salt thereof,
wherein,
$R_2$ is H, nitro, halo, an optionally substituted alkyl, an optionally substituted alkenyl, an optionally substituted aryl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;
$R_4$ is H, nitro, halo, an optionally substituted alkyl, an optionally substituted alkenyl, an optionally substituted aryl, an optionally substituted heteroaryl, optionally substituted heterocycloalkyl, $NR_AR_A$, $NHR_A$, $OR_A$, $SOR_A$, $SO_2R_A$, $SO_3R_A$, or $SR_A$;
$R_3$ is H, $C(O)R_B$, $C(O)OR_B$, $C(O)NHR_B$, $C(O)NR_BR_B$, an optionally substituted alkyl, an optionally substituted alkenyl, an optionally substituted aryl, an optionally substituted aralkyl, an optionally substituted heteroaryl, or optionally substituted heterocycloalkyl;
each $R_A$ is independently H, an optionally substituted alkyl, an optionally substituted aryl, an optionally substituted aralkyl, an optionally substituted heteroaryl, or optionally substituted heterocyclic; and
each $R_B$ is independently H, an optionally substituted alkyl, an optionally substituted aryl, an optionally substituted aralkyl, an optionally substituted heteroaryl, or optionally substituted heterocyclic.

In other embodiments, the invention provides a method as described above further comprising an additional therapeutic agent. In a further embodiment, the additional therapeutic agent is an angiogenesis-inhibiting compound. In certain embodiments, the additional therapeutic agent is a methionine aminopeptidase inhibiting compound. In other embodiments, the additional therapeutic agent is a SirT1 inhibiting compound. In other embodiments, the additional therapeutic agent is an anticancer compound.

In certain embodiments, the invention provides a method as described above wherein the step of administering the compound comprises administering the compound orally, topically, parentally, intravenously or intramuscularly.

In a further embodiment, the step of administering the compound comprises administering the compound in a dosage of between about 0.1 and 120 mg/kg/day. In certain embodiments, the step of administering the compound comprises administering the compound in a dosage of less than about 500 mg/day.

In various embodiments of the methods of the invention, the subject is a human.

In other aspects, the invention provides the use of a compound in the manufacture of a medicament for inhibiting type 2 methionine aminopeptidase in a patient, wherein the compound is a compound of formula I.

In another aspect, the invention provides the use of a compound in the manufacture of a medicament for inhibiting SirT1 in a patient, wherein the compound is a compound of formula I.

In certain aspects, the invention provides the use of a compound in the manufacture of a medicament for inhibiting angiogenesis in a patient, wherein the compound is a compound of formula I.

In certain aspects, the invention also provides for a pharmaceutical composition comprising a compound of formula I and a pharmaceutically suitable excipient.

In other aspects, the invention provides a kit comprising an effective amount of a compound of formula I in unit dosage form, together with instructions for administering the compound to a subject suffering from or susceptible to a methionine aminopeptidase-related, SirT1-related, or angiogenesis-related disease.

Diseases or disorders treated, ameliorated or prevented by the instant invention include the following: neoplasia, internal malignancies such as eye or ocular cancer, rectal cancer, colon cancer, cervical cancer, prostate cancer, breast cancer and bladder cancer, benign and malignant tumors, including various cancers such as, anal and oral cancers, stomach, rectal, liver, pancreatic, lung, cervix uteri, corpus uteri, ovary, prostate, testis, renal, mouth/pharynx, esophageal, larynx, kidney, brain/cns (e.g., gliomas), head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, lymphoma, neurofibromatosis, tuberous sclerosis (each of which conditions produces benign tumors of the skin), hemangiomas, lymphangiogenesis, rhabdomyosarcomas, retinoblastoma, osteosarcoma, acoustic neuroma, neurofibroma, trachoma, pyogenic granulomas, and blood-born tumors such as leukemias.

Other disorders treated by the compounds of the invention include any of various acute or chronic neoplastic diseases of the bone marrow in which unrestrained proliferation of white blood cells occurs, usually accompanied by anemia, impaired blood clotting, and enlargement of the lymph nodes, liver, and spleen, psoriasis, acne, rosacea, warts, eczema, neurofibromatosis, Sturge-Weber syndrome, venous ulcers of the skin, tuberous sclerosis, chronic inflammatory disease, arthritis, lupus, scleroderma, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium, keratitis sicca, Sjogren's, phylectenulosis, syphilis, Mycobacteria infections, lipid degeneration, chemical burns, bacterial ulcers, fungal ulcers, herpes simplex infections, herpes zoster infections, protozoan infections, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotmy, corneal graft rejection, diabetic retinopathy, macular edema, macular degeneration, sickle cell anemia, sarcoid, pseudoxanthoma elasticum, Paget's disease, vein occlusion, artery occlusion, carotid obstructive disease, chronic uveitis/vitritis, Lyme disease, systemic lupus erythematosus, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, rubeosis (neovascularization of the ankle), diseases caused by the abnormal proliferation of fibrovascular or fibrous tissue including all forms of proliferative vitreoretinopathy, whether or not associated with diabetes, neovascular disease, pannus, diabetic macular edema, vascular retinopathy, retinal degeneration, inflammatory diseases of the retina, proliferative vitreoretinopathy, diseases associated with rubeosis (neovascularization of the ankle), diseases caused by the abnormal proliferation of fibrovascular or fibrous tissue including all forms of proliferative vitreoretinopathy, Crohn's disease and ulcerative colitis, sarcoidosis, osteoarthritis, inflammatory bowel diseases, skin lesions, Osler-Weber-Rendu disease, or hereditary hemorrhagic telangiectasia, osteoarthritis, Sarcoidosis, skin lesions, acquired immune deficiency syndrome, and small bowel obstruction.

The inhibition of angiogenesis in treating or reversing the disease state or condition is an important aspect of the present invention. More particularly, the present invention relates to methods for inhibiting the growth of neoplasia, including a malignant tumor or cancer comprising exposing the neoplasia to an inhibitory or therapeutically effective amount or concentration of at least one of the disclosed compounds. This method may be used therapeutically, in the treatment of neoplasia, including cancer or in comparison tests such as assays for determining the activities of related analogs as well as for determining the susceptibility of a patient's cancer to one or more of the compounds according to the present invention. Treatment of internal malignancies such as eye or ocular cancer, rectal cancer, colon cancer, cervical cancer, prostate cancer, breast cancer and bladder cancer, among numerous others, and oral malignancies are also contemplated by the present invention.

Angiogenesis inhibiting compounds of the present invention are used to treat, ameliorate or prevent benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Angiogenesis is prominent in solid tumor formation and metastasis. Angiogeneic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention or control of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means can lead to cessation of the recurrence of the tumors.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenic disease, angiogenic disorder and angiogenic skin disorder are used throughout the specification to describe a disorder, generally a skin disorder or related disorder which occurs as a consequence of or which results in increased vascularization in tissue. Any skin disorder which has as a primary or secondary characterization, increased vascularization, is considered an angiogenic skin disorder for purposes of the present invention and is amenable to treatment with compounds according to the present invention.

Methods for treating, ameliorating, or preventing angiogenic skin disorders such as psoriasis, acne, rosacea, warts, eczema, hemangiomas, lymphangiogenesis, neurofibromatosis, Sturge-Weber syndrome, venous ulcers of the skin, tuberous sclerosis, chronic inflammatory disease and arthritis, as well as inflammation such as chronic inflammatory disease, including arthritis, lupus and scleroderma are also contemplated by the present invention, such methods comprising administering a therapeutically effective amount of one or more of the disclosed compounds to a patient in need of such treatment.

Diseases associated with neovascularization include optic disc neovascularization, iris neovascularization, retinal neovascularization, choroidal neovascularization, corneal neovascularization, and intravitreal neovascularization.

Diseases associated with corneal neovascularization and retinal/choroidal neovascularization that can be treated, ameliorated, or prevented, according to the present invention include but are not limited to, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, macular edema, macular degeneration, sickle cell anemia, sarcoid, syphilis, pseudoxanthoma elasticum, Paget's disease, vein occlusion, artery occlusion, carotid obstructive disease, chronic uveitis/ vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle), diseases caused by the abnormal proliferation of fibrovascular or fibrous tissue including all forms of proliferative vitreoretinopathy, whether or not associated with diabetes, and corneal graft rejection.

In some embodiments, the corneal neovascularization to be treated or inhibited is caused by trauma, chemical burns or corneal transplantation. In other particular embodiments, the iris neovascularization to be treated or inhibited is caused by diabetic retinopathy, vein occlusion, ocular tumor or retinal detachment. In still other particular embodiments, the retinal or intravitreal neovascularization to be treated or inhibited is caused by diabetic retinopathy, vein occlusion, sickle cell retinopathy, retinopathy of prematurity, retinal detachment, ocular ischemia or trauma. Additional diseases associated with choroidal neovascularization to be treated or inhibited are caused by retinal or subretinal disorders of age-related macular degeneration, diabetic macular edema, presumed ocular histoplasmosis syndrome, myopic degeneration, angioid streaks or ocular trauma.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium.

Diseases associated with chronic inflammation and arthritis can be treated, ameliorated or prevented by the compositions and methods of the present invention. Diseases with symptoms of chronic inflammation include inflammatory bowel diseases such as Crohn's disease and ulcerative colitis, psoriasis, sarcoidosis, rheumatoid arthritis, osteoarthritis, lupus and scleroderma. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state.

The compositions and methods of the present invention can be used to treat, ameliorate or prevent disease in patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease is active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease (or symptoms thereof) which can be treated, ameliorated or prevented according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Another disease that can be treated according to the present invention are Osler-Weber-Rendu disease, or hereditary hemorrhagic telangiectasia, and acquired immune deficiency syndrome.

Factors associated with angiogenesis may also have a role in osteoarthritis. The activation of the chondrocytes by angiogeneic-related factors contributes to the destruction of the joint. At a later stage, the angiogeneic factors would promote new bone formation. Therapeutic intervention that prevents the bone destruction could halt the progress of the disease and provide relief for persons suffering with arthritis.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula, thereby preventing conception.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

The present compounds may be used to treat subjects including animals, and in particular, mammals, including humans, as patients. Thus, humans and other animals, and in particular, mammals, suffering from diseases or disorders related to hMetAP and/or angiogenesis, can be treated, ameliorated or prevented by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents (depending upon the disease to be treated). Treatment according to the present invention can also be administered in conjunction with other conventional therapies, e.g., cancer therapy, such as radiation treatment or surgery.

The compounds of the invention may be utilized in combination with at least one known other therapeutic agent, or a pharmaceutically acceptable salt of said agent. Examples of known therapeutic agents which can be used for combination therapy include, but are not limited to, corticosteroids (e.g., cortisone, prodnisone, dexamethasone), non-steroidal anti-inflammatory drugs (NSAIDS) (e.g., ibuprofen, celecoxib, aspirin, indomethicin, naproxen), alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

IV. Mechanism of Action

Nitroxoline was Identified as a Common Hit from Three Independent Screenings of Anti-Angiogenic and Anti-Cancer Drugs To discover clinically feasible anti-angiogenic and anti-cancer drugs, three independent drug screenings were conducted, including human methionine aminopeptidase type-2 (MetAP-2) inhibitors from ~170,000 commercial chemical library, endothelial cell growth inhibitors from ~4,500 clinical drug library, and anti-breast cancer drugs from ~2,300 FDA-approved drug library. MetAP-2 screening was conducted using the high throughput automatic screening systems. Cell growth inhibitor screenings were conducted through the method based on the 3H-thymidine incorporation assay. A large number of hits were isolated from each screening; i.e. hits from endothelial inhibitor screening (Curtis, R. C. et al (2007) ACS Chem. Biol. 2, 263-270), 212 hits from anti-breast cancer drug screening, and hits from MetAP-2 inhibitor screening (published elsewhere). Interestingly, an anti-bacterial drug, nitroxoline was discovered as a common hit from those three independent screenings.

Nitroxoline Inhibits MetAP-2 Activity and the Proliferation of Both Endothelial and Breast Cancer Cells The effect of nitroxoline on the activity of MetAPs in the presence of two different physiological cofactors was examined. Nitroxoline specifically inhibited MetAP-2 activity in the presence of $Mn^{2+}$ with an $IC_{50}$ value of 460 nM (FIG. 1, Table 1, left panel). Nitroxoline also inhibited the MetAP-2 activity in the presence of $Co^{2+}$, but the potency was 25-fold lower than that in the case of $Mn^{2+}$. MetAP-1 activity was, however, not inhibited at all by nitroxoline regardless of metal ion presence. IV-43 and TNP-470 were used as positive control compounds for MetAP-1 and MetAP-2 inhibitors, respectively.

Cell proliferation assay was performed using several different kinds of breast cancer cells as well as human umbilical vein endothelial cells (HUVECs). Nitroxoline inhibited the proliferation of all the cell types with $IC_{50}$ ranges from 2 to 5 µM. Considering the fact that TNP-470 has an endothelial selectivity of around 1,000-fold over other types of cancer cell lines, nitroxoline does not have cellular selectivity (FIG. 1, Table 1, right panel).

Nitroxoline Inhibits MetAP-2 Activity In Vivo

To verify the effect of nitroxoline on MetAP-2 in the physiological environment, mutant yeast cell growth assays were conducted. Since, two eukaryotic MetAPs are functionally complemental to each other, the yeast can survive under the genetic deficiency of one of MetAP isotypes. The treatment of wild-type yeast with nitroxoline or TNP-470 did not inhibit the yeast growth. The growth of MetAP-1 deletion mutant (map1Δ), however, was significantly inhibited by either nitroxoline or TNP-470. The treatment with nitroxoline or TNP-470 did not affect the growth of MetAP-2 deletion mutant which does not have their cognate target, suggesting that MetAP-2 is a physiological target of both nitroxoline and TNP-470 (FIG. 2A).

Figure 2B:
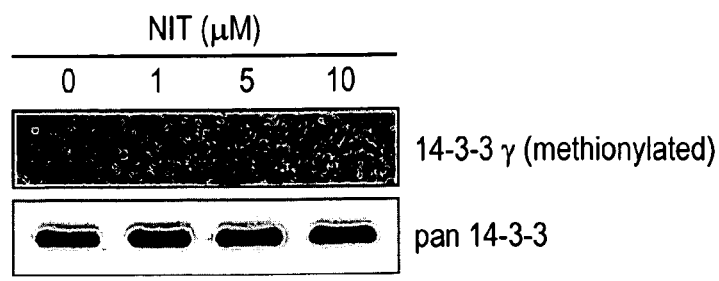

14-3-3γ is known as a substrate of eukaryotic MetAPs and the inhibition of either isotype of MetAPs was reported to increase the N-terminal methionyl form of the protein. As expectedly, the treatment of HUVECs with nitroxoline dose-dependently increased the N-terminal methioninylated 14-3-3γ, which was detected by N-methionyl 14-3-3γ-specific antibody (FIG. 2). To estimate how much portion of total 14-3-3γ is unprocessed by nitroxoline, we knocked down the expression of endogenous hMetAP2 using a specific siRNA and analyzed the processing of 14-3-3γ in HUVECs. As low as 5 nM of hMetAP2 siRNA treatment for 48 h induced over 90% knock-down of hMetAP2 as shown by the western blot (FIG. 2). The unprocessed form of 14-3-3 γ was significantly increased after knock down of hMetAP2. Compared with hMetAP2 siRNA, 5 µM nitroxoline inhibited the processing of 14-3-3 γ by ~80%. TNP-470 completely blocked the processing of 14-3-3γ by hMetAP2 at 10 nM (FIG. 2). These results demonstrate that nitroxoline inhibits hMetAP2 activity in vivo. As the $IC_{50}$ of nitroxoline for the inhibition of hMetAP1 is above 50 µM, inhibition of this enzyme cannot account for the retention of the N-terminal methionine in 14-3-3γ.

Nitroxoline Activates p53 and Rb Pathways in HUVECs

Figure 3A:
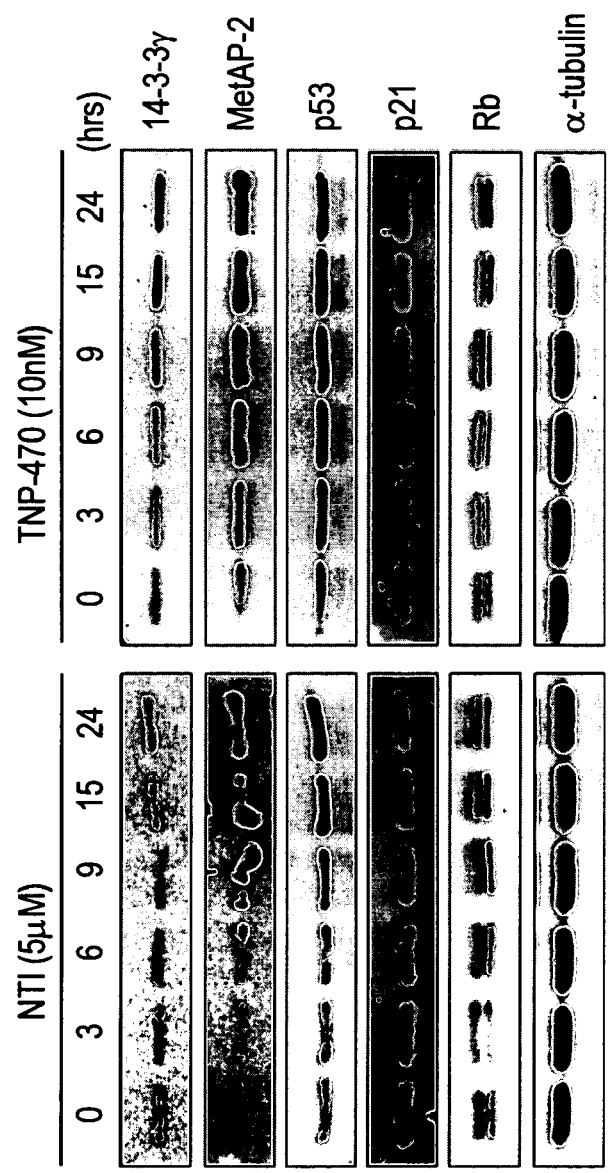
FIG. 3. Mechanism of inhibition of endothelial cell proliferation by nitroxoline. A, Effects of MetAP inhibitors on the protein level of MetAP-2 and p53 in HUVECs in different time points. HUVECs were treated with MetAP2 inhibitors for indicated time points and Western blot was conducted using specific antibodies against each protein of interest. α-Tubulin protein level was used as an internal control. Rb (12%) and Rb (8%) represent Western blots of Rb after running with 12% and 8% of SDS-PAGE, respectively. B, Cell cycle distribution of HUVECs after treatment with nitroxoline or TNP-470 for 24 h. Quantification of cell cycle distribution in each condition was conducted using the Cell Quest software.
Figure 3B:
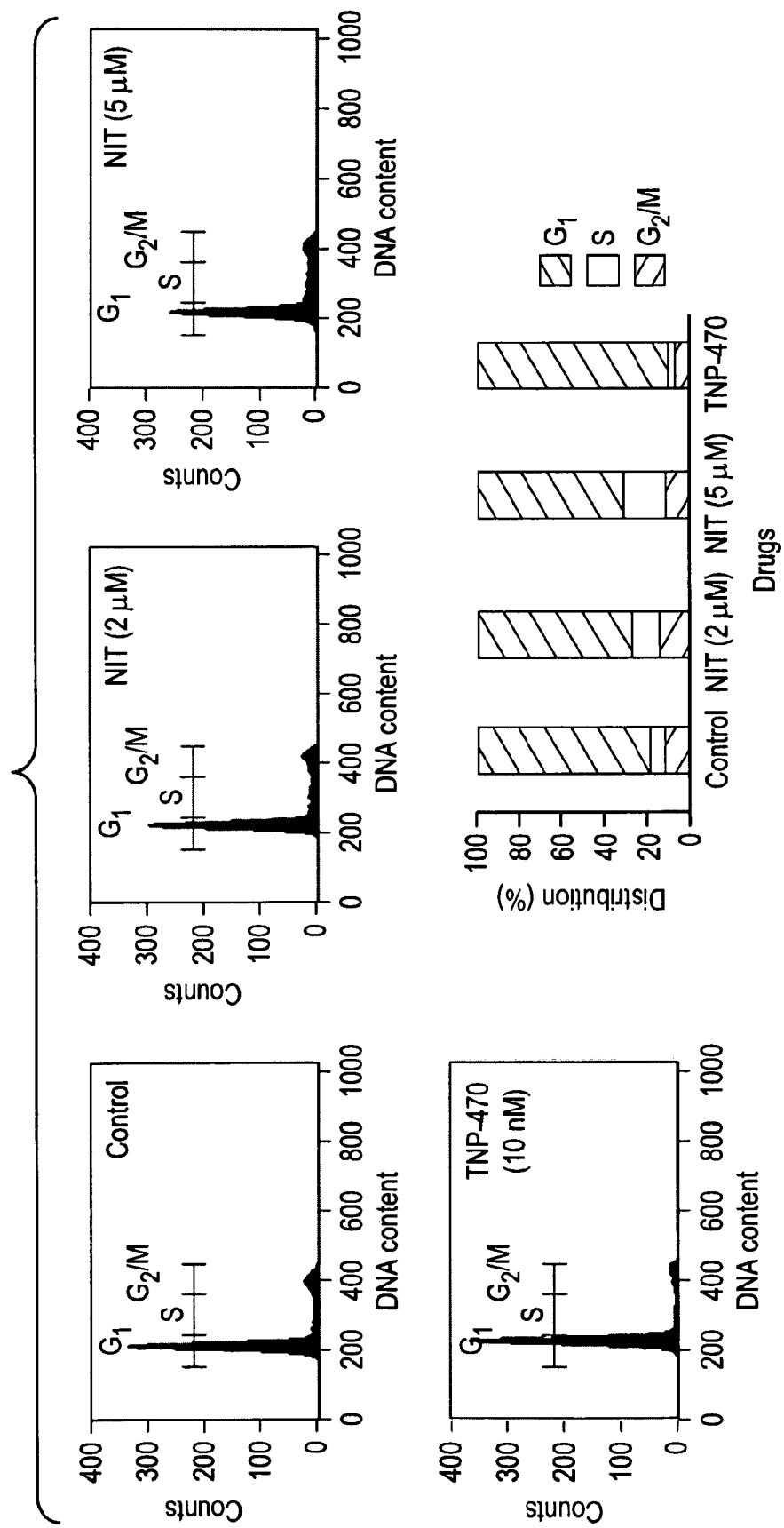
Figure 4B:
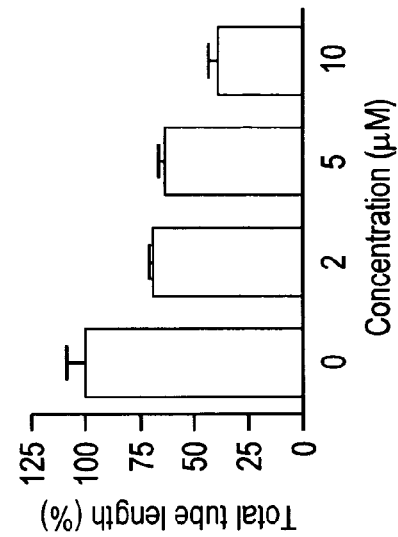
FIG. 4. Effects of nitroxoline on angiogenesis in vitro and in vivo. A, HUVECs growing on Matrigel formed tube-like structures in the presence of angiogenic factors. The tubular structures were stained with calcein-AM for 30 min and observed under a fluorescent microscope. B, AngioQuant image analysis software was used for the quantitative analysis of the experiments. C. In vivo Matrigel plug assay was performed using nude mice (n=5/group). Matrigels were extracted from the mice and the representative ones were photographed. D, Matrigels were fixed with PBS-buffered 10% formalin containing 0.25% glutaraldehyde for 48 hours at room temp, and processed for Masson's Trichrome staining. Blood vessels which contained red blood cells inside of them were counted and quantified.
Figure 4D:
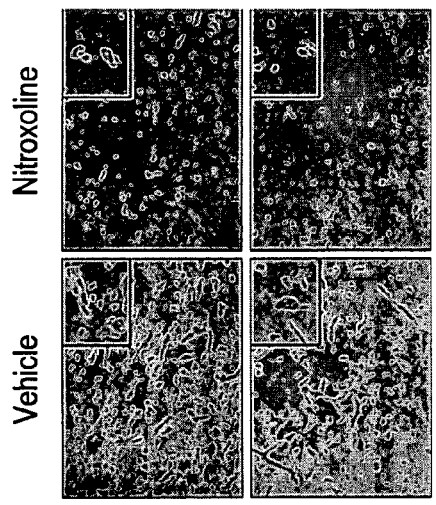
Figure 4A:
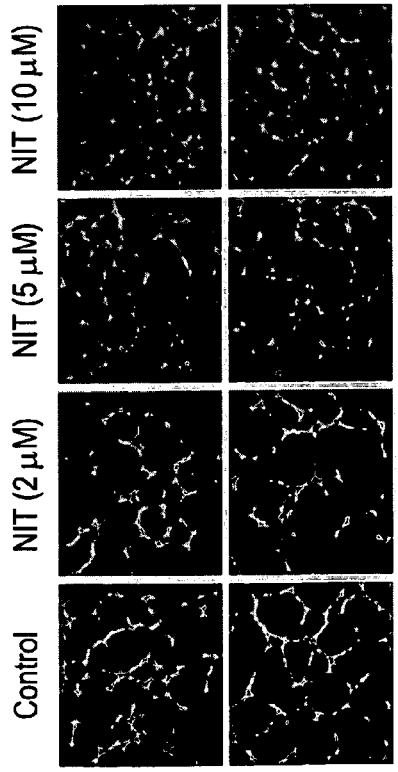
Figure 4C:
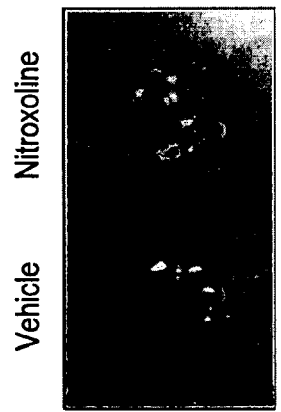

It has been previously shown that the cell cycle effect of TNP-470 is mediated through the activation of the p53 pathway, which is accompanied by upregulation of p21 and inhibition of Rb hyperphosphorylation by the cyclinE/Cdk2 kinase complex (Zhang, Y. et al (2000) *Proc. Natl. Acad. Sci. U. S. A.*, 97, 6427-6432; Yeh, J. R. et al (2000) *Proc. Natl. Acad. Sci. U.S.A.* 97, 12782-12787). Similar to TNP-470, nitroxoline treatment also led to upregulation of p53 protein level (FIG. 3A). In contrast to TNP-470, however, nitroxoline had no effect on the expression of p21 within 24 h of treatment. In addition, both nitroxoline and TNP-470 increased the total amount of Rb protein (shown in 12% of SDS-PAGE) and inhibited its hyperphosphorylation, leading to the accumulation of the hypophosphorylated Rb over time (shown in 8% of SDS-PAGE). Interestingly, prolonged exposure (up to 72 h) of HUVEC to nitroxoline induced sustained increase in p53 protein level. Similarly, the protein level of p21 was upregulated upon longer incubation of the endothelial cells with nitroxoline (FIG. 3). At the mRNA level, however, p53 was decreased, while p21 was increased upon treatment with nitroxoline in a time-dependent manner. These data indicate that although nitroxoline reduced p53 transcription upon prolonged treatment, it increased the protein stability and transcriptional activity of p53 in HUVEC.

Nitroxoline Induces Premature Senescence in Endothelial Cells.

HUVEC that was treated with nitroxoline, but not with TNP-470, underwent morphological changes similar to those upon extended passage in culture. It is known that primary endothelial cell culture become senescent upon repeated passages in culture, a process referred to as replicative senescence. Senescence can also occur in response to acute stresses, such as UV irradiation or chemotherapeutic drug treatment, which is referred to as stress-induced premature senescence. The morphological change caused by nitroxoline which was accompanied by premature senescence using a cell-permeable senescence-associated β-galactosidase (SA-β-gal) substrate, was then determined. Treatment of HUVEC with 0.1 mM valproic acid, a known histone deacetylase inhibitor used as a positive control, for 72 h induced premature senescence in HUVEC. Similar to valproic acid, nitroxoline also induced premature senescence in HUVEC. At 20 nM, a concentration that is sufficient to inhibit HUVEC proliferation, however, TNP-470 did not induce premature senescence. Next tested was whether senescence induced by nitroxoline is reversible. HUVEC were treated with nitroxoline for 72 h and the culture media containing nitroxoline was replaced with fresh media followed by incubation for an additional 48 h. Judged from SA-β-gal staining, nitroxoline-treated HUVEC (nitroxoline-R) remained senescent while those treated with valproic acid (valproic acid-R) reversed their senescence state. These results demonstrate that, unlike TNP-470, nitroxoline induced sustained premature senescence in HUVEC. Since nitroxoline is cytostatic rather than cytotoxic to endothelial cells, activation of p53, p21 and inhibition of Rb pathway are likely to be involved in the induction of premature senescence in endothelial cells.

Nitroxoline Induces p53 Acetylation at K382 and Inhibits SirT1 Activity.

Figure 5A:
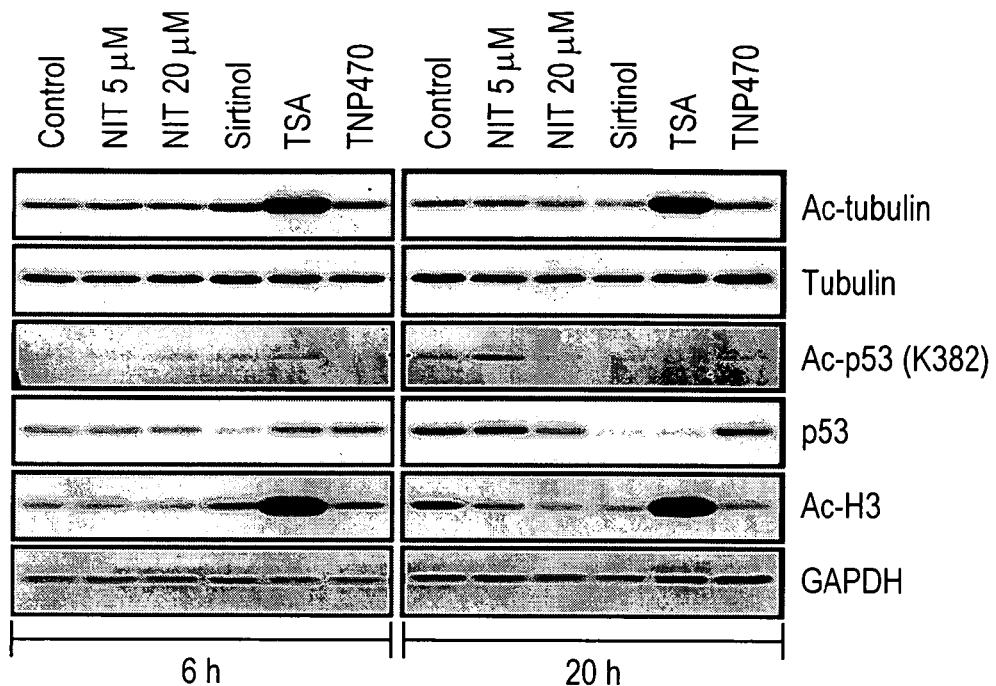
FIG. 5. Nitroxoline inhibits sirtuin activities. A, Induction of p53 acetylation at lysine 382 by nitroxoline. HUVEC were treated with nitroxoline (NIT) and other compounds for either 6 h or 20 h, and analyzed for acetylation status of p53 (K382), α-tubulin and histone-H3 using specific antibodies. B, Effect of nitroxoline on sirtuin activities. Recombinant human sirtuins and their preferred fluorogenic peptide substrates were used for the enzyme assay as described in Materials and Methods. Estimated $IC_{50}$ values of SirT1, SirT2 and SirT3 were 8.5, 35 and >50 μM, respectively. C, Dose-dependent, biphasic induction of p53 acetylation by nitroxoline. HUVEC were treated with various concentrations of nitroxoline for 20 h and acetylation status of endogenous sirtuin substrates were analyzed by Western blots. D, The level of acetylation and total p53 protein in each lane was normalized by the level of α-tubulin. Intensity of each protein band was quantitated using ImageJ software.
Figure 5B:
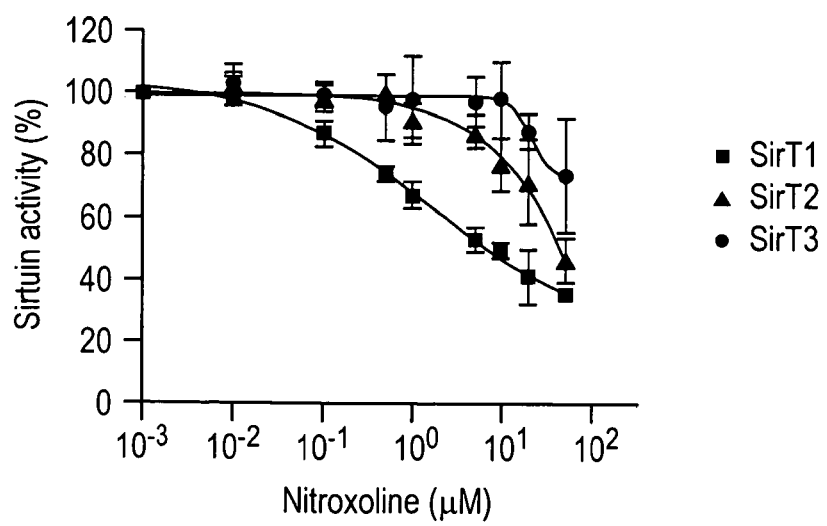
Figure 5C:
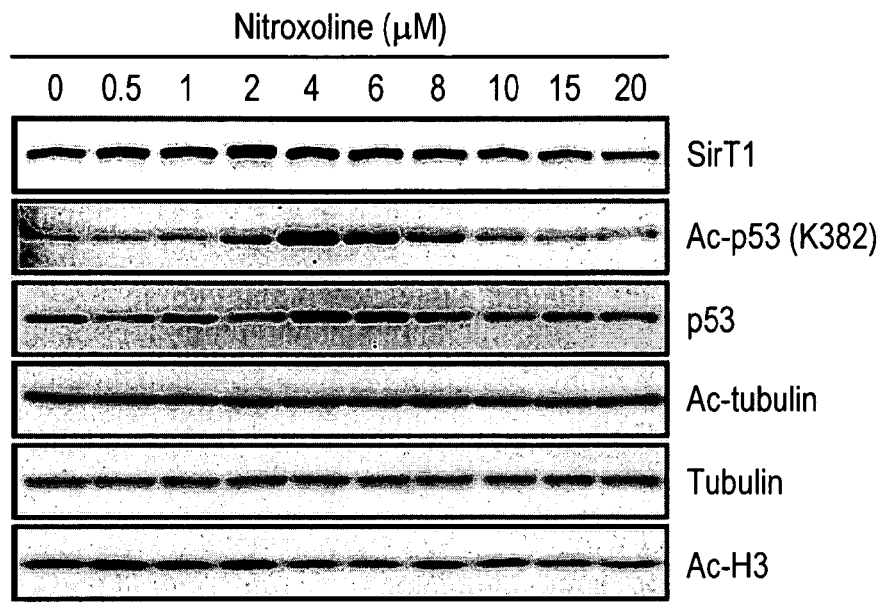
Figure 5D:
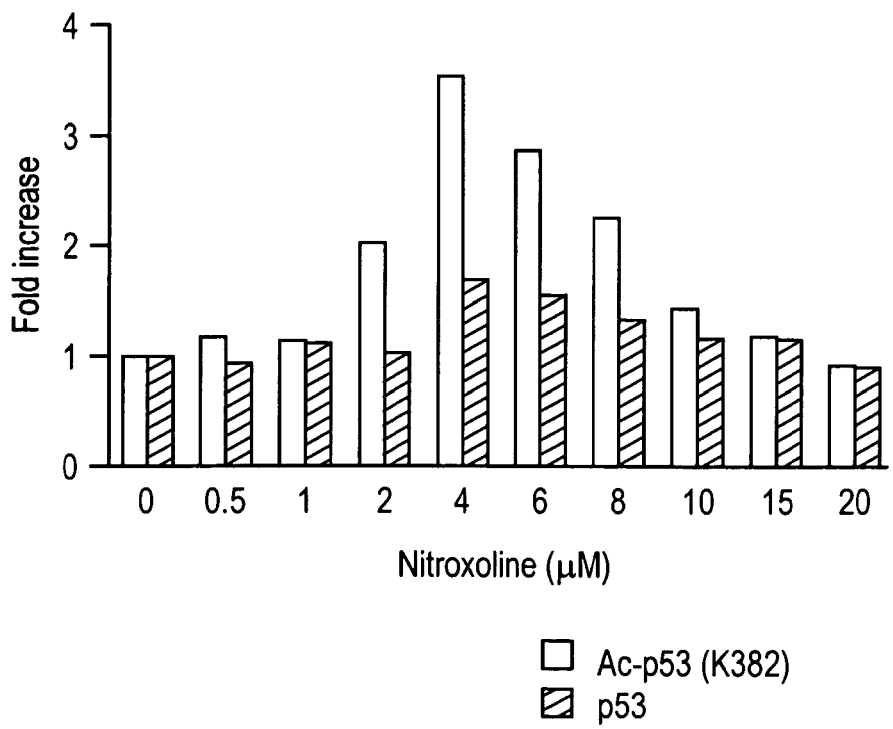
Figure 6A:
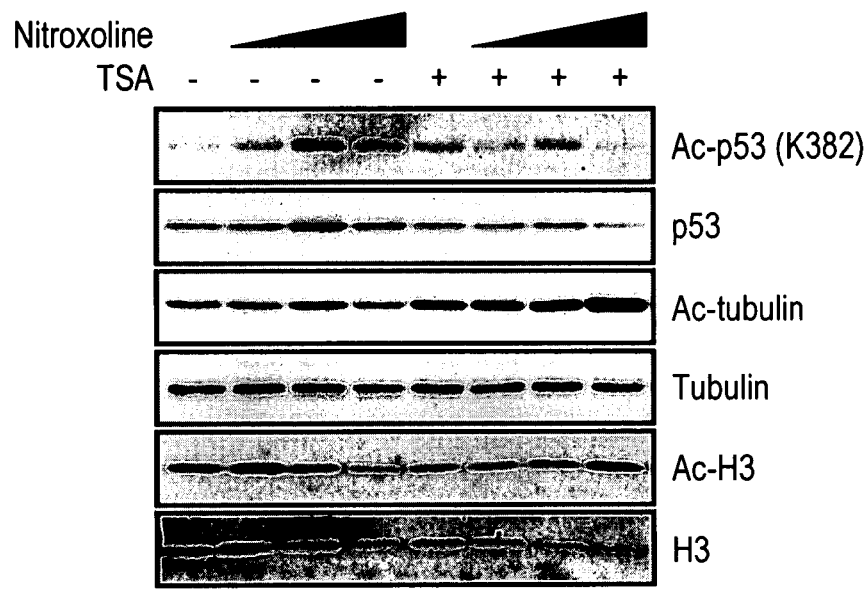
FIG. 6. Nitroxoline effect mimics the concurrent inhibition of MetAP2 and SirT1 in HUVEC. A, Effects of nitroxoline on acetylation status of various sirtuin substrates in the presence or absence of Class-I histone deacetylase inhibitor. HUVEC were treated with 0, 1, 5 and 20 μM nitroxoline with or without TSA (200 nM) for 24 h. B, HUVEC were treated with 0, 5 and 15 μM EX527 with or without TSA (200 nM) for 24 h. C, Knock-down of SirT1 and MetAP2 mimics nitroxoline effects on p53 acetylation. Two different siRNA oligos against SirT1 mRNA (siRNA#1 and #3) were introduced into HUVEC using HiperFect reagent and acetylation status of p53 (K382) and α-tubulin was analyzed by Western blot. HUVEC were transfected with designated siRNA oligos for 24 h and treated with either vehicle or compounds for an additional 24 h. Cells were then harvested for Western blot analysis. D, Pharmacological inhibition of SirT1 and MetAP2 mimics nitroxoline effects on p53 acetylation. HUVEC were treated with 0, 0.2 and 2 μM EX527 in the presence or absence of either TNP470 (10 nM) or TSA (200 nM) for 20 h. Acetylation status of p53 (K382) and α-tubulin was analyzed by Western blot.

Human sirtuin family is consisted of 7 isoforms (SirT1 through 7) whose catalytic domain is homologous to the yeast Sir2. Each isoform of human sirtuin is known to have different substrate specificity. For instance, SirT1 is known to deacetylate p53 specifically at K382 position, whereas SirT2 is reported as a tubulin deacetylase. To see if nitroxoline or the compounds of the invention induces hyper-acetylation of these sirtuin substrates, HUVEC were treated with various compounds for either short (6 h) or long (20 h) time and the acetylation status of various sirtuin substrates were analyzed. First, nitroxoline did not change the acetylation status of either tubulin or histone-H3, while sirtinol (plant sirtuin inhibitor) and TSA (class-I and -II HDAC inhibitor) induced hyper-acetylation of those substrates (FIG. 5A). Nitroxoline, however, increased the acetylation of p53-K382 in HUVEC treated for 20 h. TSA increased p53 acetylation at an early time point. Next, in vitro sirtuin assays were conducted based on deacetylation of fluorogenic substrates by purified recombinant sirtuin enzymes. Nitroxoline inhibited SirT1 activity with an $IC_{50}$ value of 8 μM (FIG. 5B). Inhibition of SirT1 by nitroxoline was relatively selective over SirT2 and SirT3 of which $IC_{50}$ values are 43 and >50 μM, respectively. As shown in FIG. 6A, high concentration of nitroxoline (20 μM) did not increase p53 acetylation. Next examined was the effect of various concentrations of nitroxoline on p53 acetylation in HUVEC. Interestingly, nitroxoline showed a biphasic induction of p53 acetylation with a peak at 4~5 μM (FIGS. 5C and D). The level of p53 itself was also increased by nitroxoline but the increasing rate was much less than that of acetylation.

Nitroxoline Effect Mimics the Concurrent Inhibition of MetAP2 and SirT1 in HUVEC.

Figure 6B:
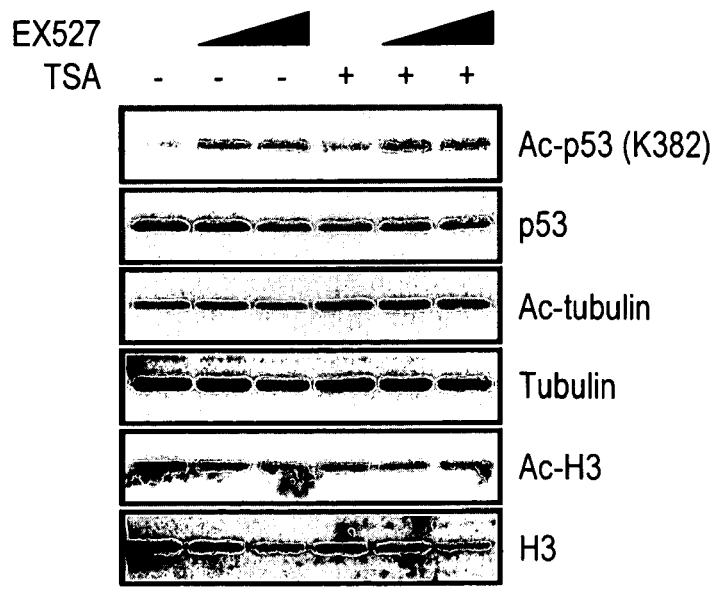
Figure 6C:
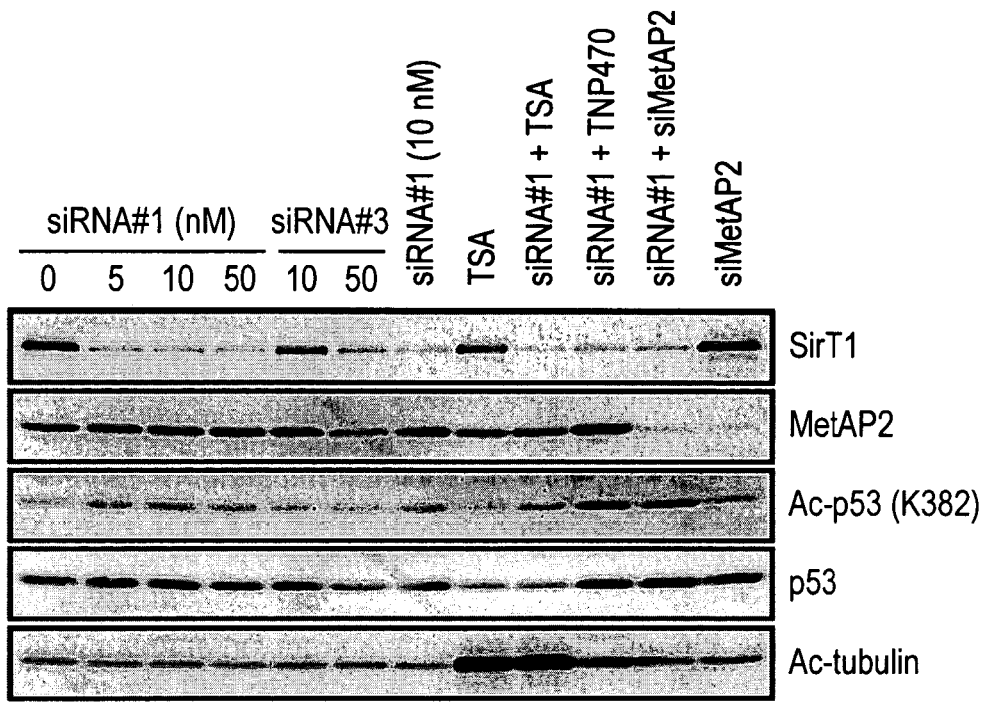
Figure 6D:
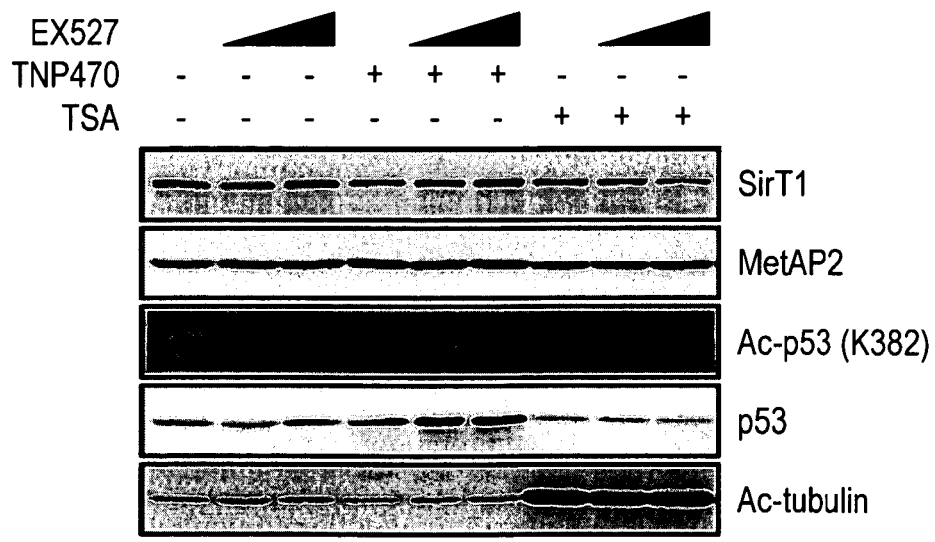

SirT2 is known to be a tubulin deacetylase (North, B. J. et al (2003) *Mol. Cell*, 11, 437-444). Pharmacological inhibition of SirT2 increases tubulin and histone acetylation in the presence of TSA (Lain, S. et al (2008) *Cancer Cell*, 13, 454-463). As shown in FIG. 6A, nitroxoline alone did not induce acetylation of either tubulin or histone-H3 in HUVEC. In the presence of TSA, however, nitroxoline at 20 μM significantly increased the acetylation of both tubulin and histone-H3, demonstrating that nitroxoline inhibits SirT2 activity at high concentration. EX527 as a known specific inhibitor of SirT1 slightly induced acetylation of p53-K382 in HUVEC. However, it did not increase acetylation of tubulin or histone-H3 even in the presence of TSA (FIG. 6B), confirming that EX527 does not inhibit SirT2 at the concentration used in this study. The effect of the concurrent inhibition of MetAP2 and SirT1 on p53 acetylation in HUVEC was examined using specific small molecule inhibitors and siRNAs. Both siRNAs against either SirT1 or MetAP2 successfully diminished the expression of each protein as confirmed by western blot. When compared with control, SirT1-siRNA slightly increased p53 acetylation (FIG. 6C). Induction of p53 acetylation by SirT1-siRNA was even increased in the presence of TNP470 or MetAP2-siRNA in HUVEC. TSA did not increase the acetylation of p53 induced by SirT1-siRNA. Similar results were obtained with small molecule inhibitors of SirT1 and MetAP2. EX527 alone slightly induced p53 acetylation while co-treatment with TNP470 significantly increased the acetylation of p53 in HUVEC (FIG. 6D). The protein level of p53 was also cooperatively increased by EX527 and TNP470.

Concurrent Inhibition of MetAP2 and SirT1 Synergistically Acts on HUVEC Proliferation and Senescence.

Figure 7A:
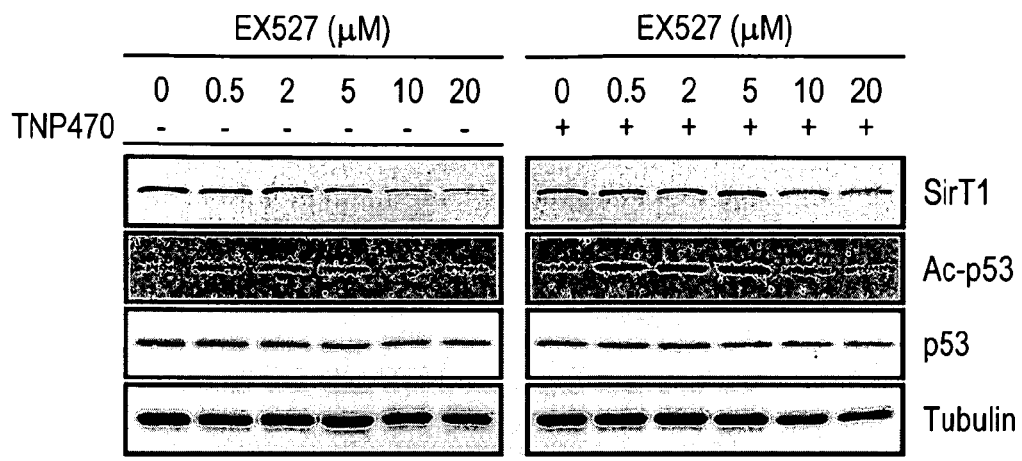
FIG. 7. Concurrent inhibition of MetAP2 and SirT1 synergistically acts on HUVEC proliferation and senescence. A, Synergistic induction of p53 acetylation by concurrent inhibition of MetAP2 and SirT1. HUVEC were treated with various concentrations of EX527 with or without 10 nM TNP470 for 24 h. The level of total p53 protein (B) and acetylation (C) in each lane was normalized by the level of α-tubulin. Intensity of each protein band was quantitated using ImageJ software. D, Effects of TNP470 and EX527 on HUVEC senescence. HUVEC were treated with each compound or drug combination for 5 days and SA-β-gal staining was conducted as described previously. E, Synergistic inhibition of HUVEC proliferation by TNP470 and EX527. The synergism between two drugs was calculated mathematically based on Chou-Talalay's Combination Index (CI) equation (CI=1, additive effect; <1, synergy, >1, antagonism). The CI values for the drug combination were obtained using the CompuSyn software. Fa represents effect value (1=100% inhibition). Each data point indicates ⅛ of $IC_{50}$, ¼ of $IC_{50}$, ½ of $IC_{50}$ and $IC_{50}$ values of two drug combinations. Data represents mean±SD from three independent experiments.
Figure 7B:
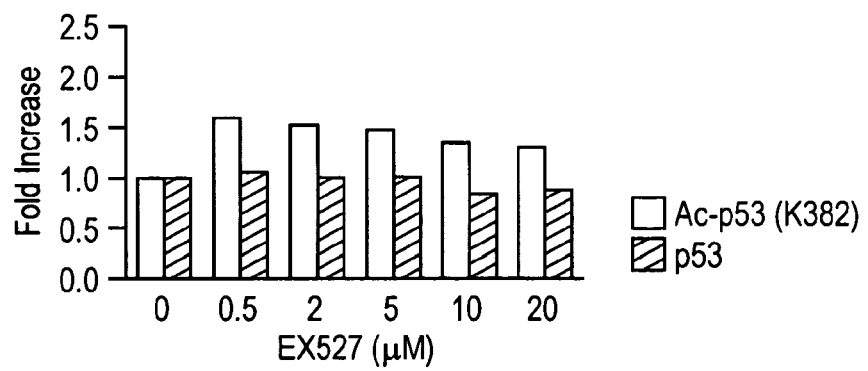
Figure 7C:
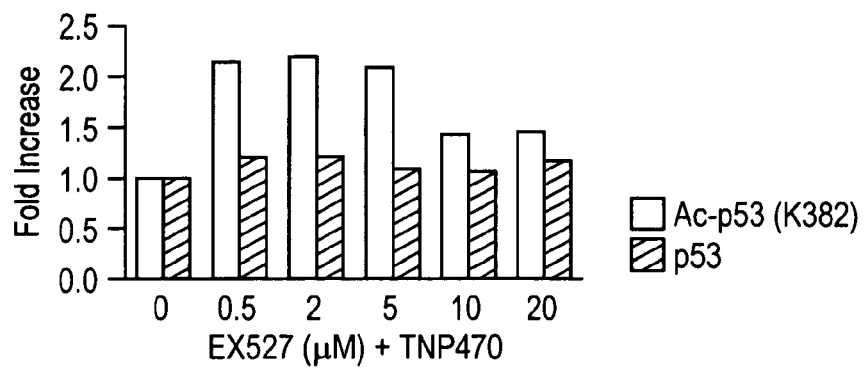
Figure 7D:
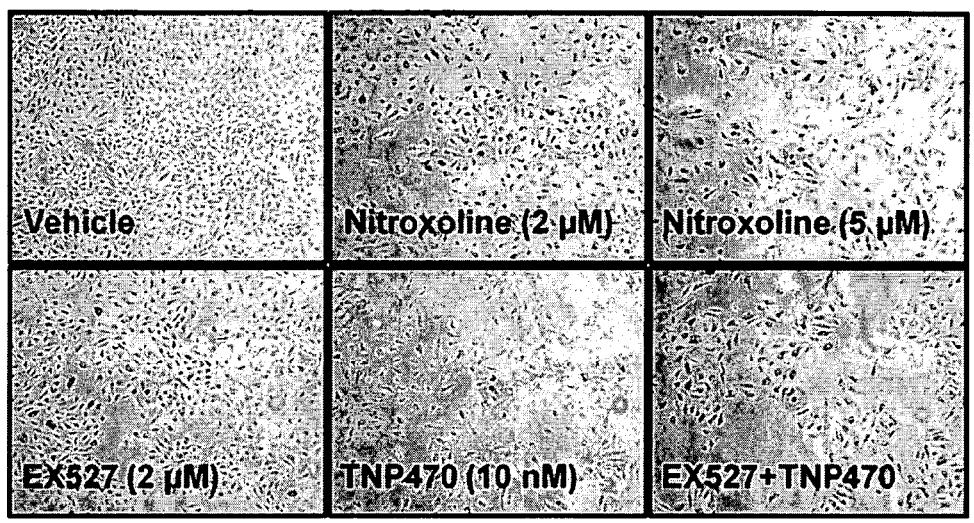
Figure 7E:
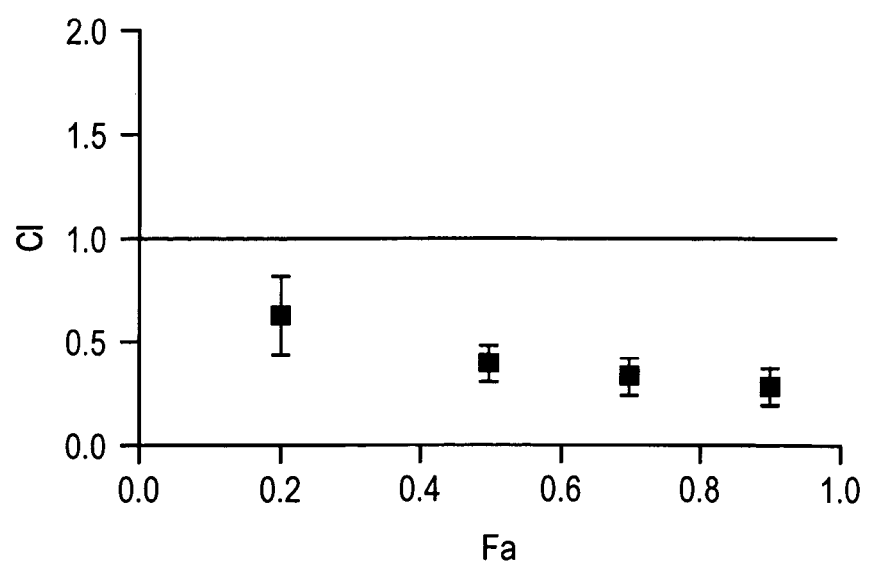

The rate of induction of p53 acetylation by nitroxoline was much higher than that of EX527, even though EX527 is highly potent inhibitor of SirT1 ($IC_{50}$=38 nM). This is probably due to the concurrent inhibition of SirT1 and MetAP2 by nitroxoline, since simultaneous inhibition of SirT1 and MetAP2 cooperatively increased the acetylation level of p53. An experiment was carried out to determine if the concurrent inhibition of MetAP2 and SirT1 synergistically acts on HUVEC proliferation and senescence. First, HUVEC were treated with various concentration of EX527 in the presence or absence of TNP470 and p53 acetylation was measured by western blot. As expected, EX527 and TNP470 synergistically induced p53 acetylation in HUVEC (FIGS. 7A-C). Like nitroxoline, the induction of p53 acetylation by EX527 alone or EX527 plus TNP470 was dose-dependent, biphasic pattern. Inhibition of SirT1 is known to induce premature senescence-like phenotype in HUVEC (Ota, H. et al (2007) J Mol Cell Cardiol., 43, 571-579). In this study, EX527 alone induced premature senescence in HUVEC, while TNP470 did not (FIG. 7D). Co-treatment of HUVEC with EX527 and TNP470 synergistically induced premature senescence in HUVEC as judged by SA-β-Gal staining. The concurrent inhibition of SirT1 and MetAP2 also showed a synergy in inhibition of HUVEC proliferation as confirmed by the Combination Index (CI) plot (FIG. 7E). These results explain why nitroxoline showed much higher potency in induction of p53 acetylation and inhibition of HUVEC proliferation than EX527 though EX527 is much more potent inhibitor of SirT1.

Nitroxoline Inhibits Angiogenesis In Vitro and In Vivo.

Figure 8A:
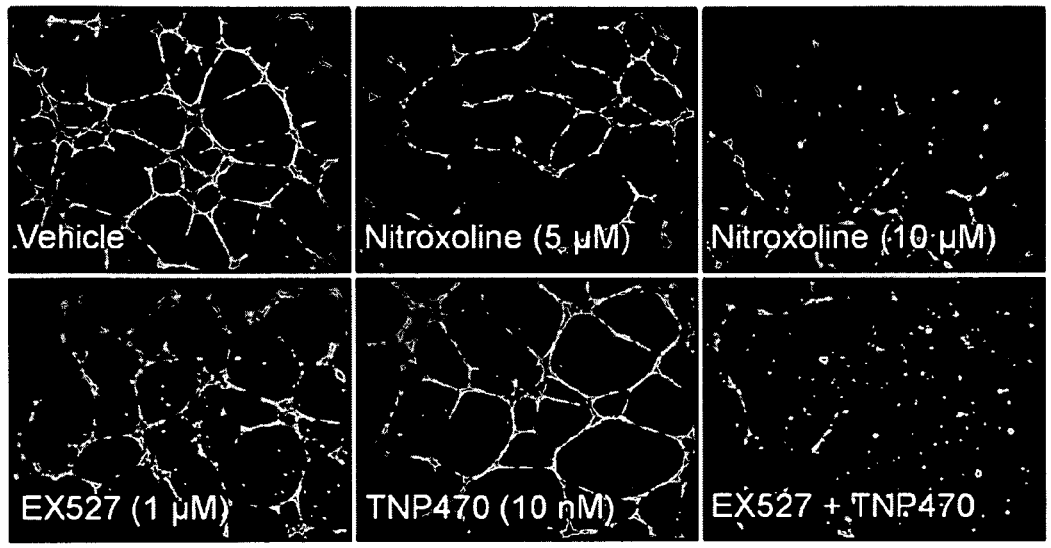
FIG. 8. Effects of nitroxoline on angiogenesis in vitro and in vivo. A, Inhibition of tube formation of HUVEC by either nitroxoline or drug combination of MetAP2 and SirT1 inhibitors in vitro. HUVEC were placed on pre-solidified Matrigel in the presence or absence of each compound and were incubated for 24 h. The tubular structures were stained with calcein-AM and observed under a fluorescent microscope. B, Total tube length was quantified using the AngioQuant image analysis software. C, In vivo Matrigel plug assay was performed using female athymic nude mice. The mice (n=5/group) were treated with either vehicle or nitroxoline (60 mg/kg/day) for 10 days via i.p. injection. Matrigel plugs were then extracted from the mice and stained with MAS-Trichrome. Representative Matrigel plugs were shown macroscopically (C) and microscopically (D). Arrowheads indicate erythrocyte-filled blood vessels. E, Blood vessels from the Matrigel plugs were counted and quantified under a phase contrast microscope. *P≤0.001 vs vehicle control.
Figure 8B:
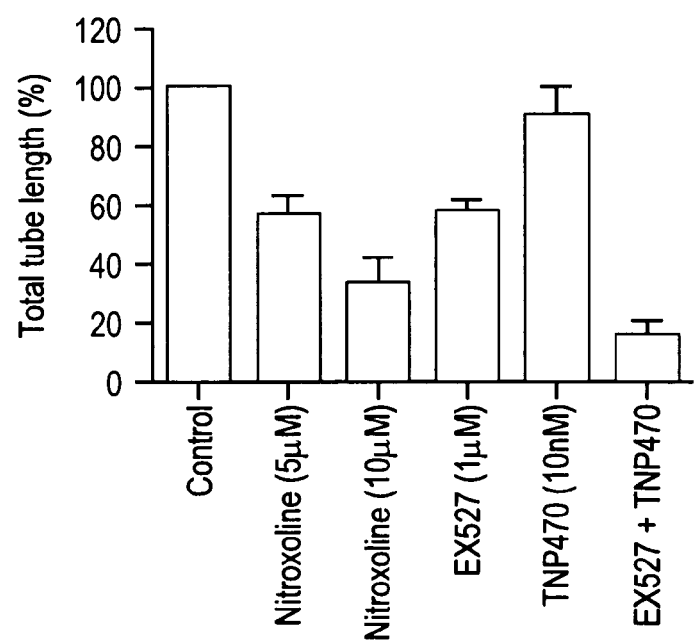
Figure 8C:
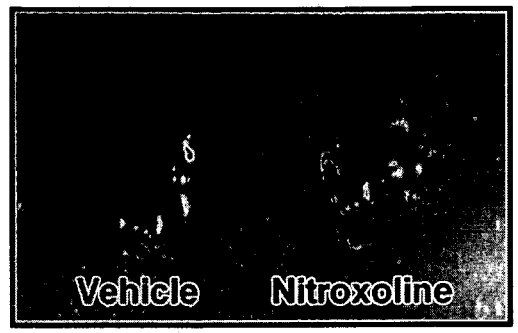
Figure 8D:
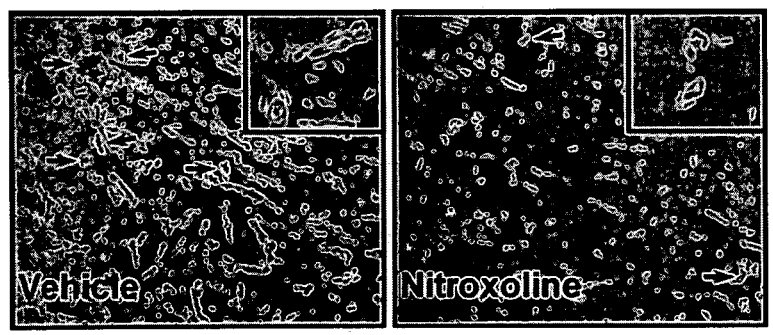
Figure 8E:
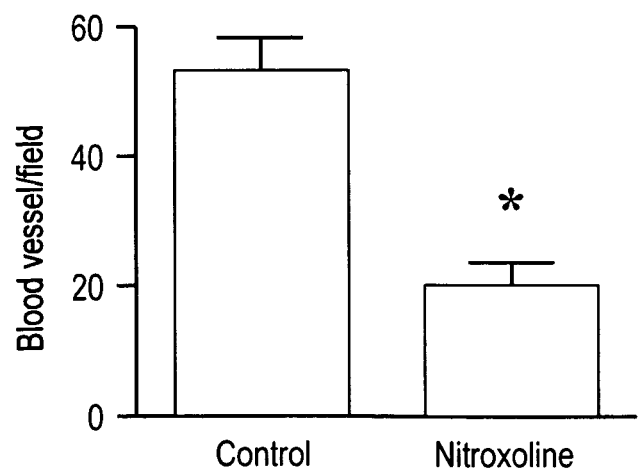

To determine whether nitroxoline is effective in blocking angiogenesis, we first employed a tube formation assay in vitro. When cultured in a three-dimensional matrigel, HUVEC form tubular structures reminiscent of vessels. The HUVEC tube formation was inhibited by nitroxoline in a dose-dependent manner (FIG. 8A). Previously, it is known that SirT1 inhibition can sufficiently suppress angiogenesis in vitro and in vivo (Potente, M. et al (2007) Genes Dev., 21, 2644-2658). It is not surprising that EX527 (1 µM) inhibited the tube formation (FIG. 8A). TNP470, however, did not inhibit tube formation at 10 nM concentration at which the compound can sufficiently inhibit HUVEC proliferation. TNP470 seems to act on G1 cell cycle progression in endothelial cells, thereby inhibiting the cell proliferation. Since tube formation requires endothelial cell differentiation but not proliferation, TNP470 is likely to have no effect on the tube formation of endothelial cells. However, combined treatment of HUVEC with EX527 and TNP470 synergistically inhibited tube formation of HUVEC (FIGS. 8A and B). Next, the efficacy of nitroxoline was determined in blocking angiogenesis in a Matrigel model in vivo. Matrigel containing basic FGF and VEGF was injected subcutaneously into mice, which were pre-treated with either vehicle control or nitroxoline. Ten days after initial injection, the Matrigel plugs were removed and the newly invaded blood vessels were visualized microscopically (FIG. 8C). In comparison to vehicle-treated animals, those that were treated with nitroxoline at 60 mg/kg had a dramatic reduction in the density of new blood vessels (FIGS. 8D and E).

Inhibition of Breast Cancer Xenograft by Nitroxoline In Vivo.

Figure 9A:
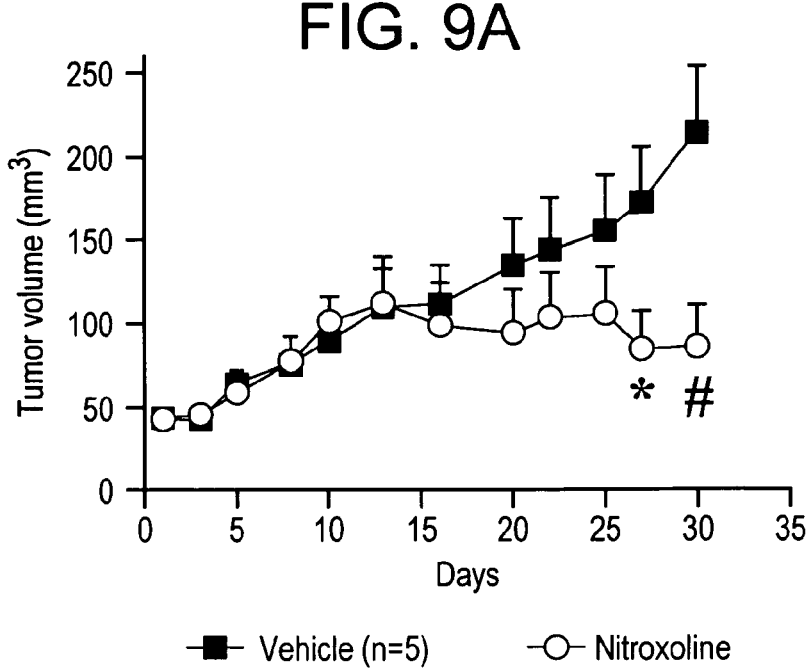
FIG. 9. Effects of nitroxoline on xenograft tumor growth and angiogenesis. A, HCC1954 human breast cancer cells were transplanted into female athymic nude mice. After tumors became palpable, mice were treated with either vehicle or nitroxoline (60 mg/kg) via i.p. injection every other day. The tumor volume was measured every three days as described in Methods. *P=0.034 and #P=0.012 vs vehicle control. B, Average weights of tumors from vehicle and nitroxoline-treated mice were shown. *P=0.036 vs vehicle control. C, Total p53 level and acetylation status of p53 (K382) in tumor samples from vehicle control and nitroxoline-treated groups are shown by Western blot. D, Immunohistochemical (IHC) staining of CD31 in the tumor tissue sections was shown. MOCK represents the IHC without primary antibody (CD31). E, Total number of blood vessels present in the IHC data was quantified by counting the number of stained vessels per field. *P=0.04 vs vehicle control.
Figure 9B:
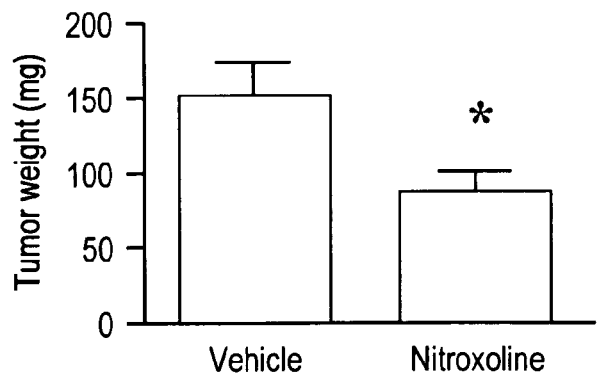
Figure 9C:
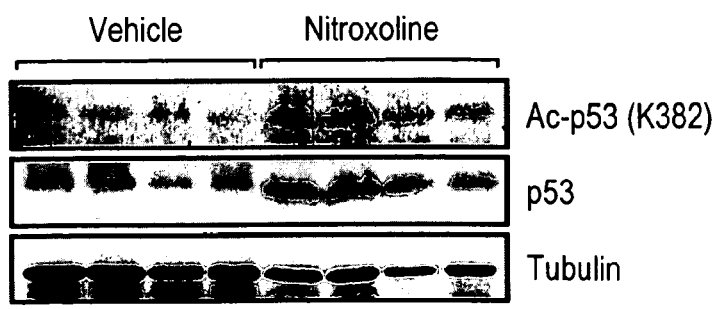
Figure 9D:
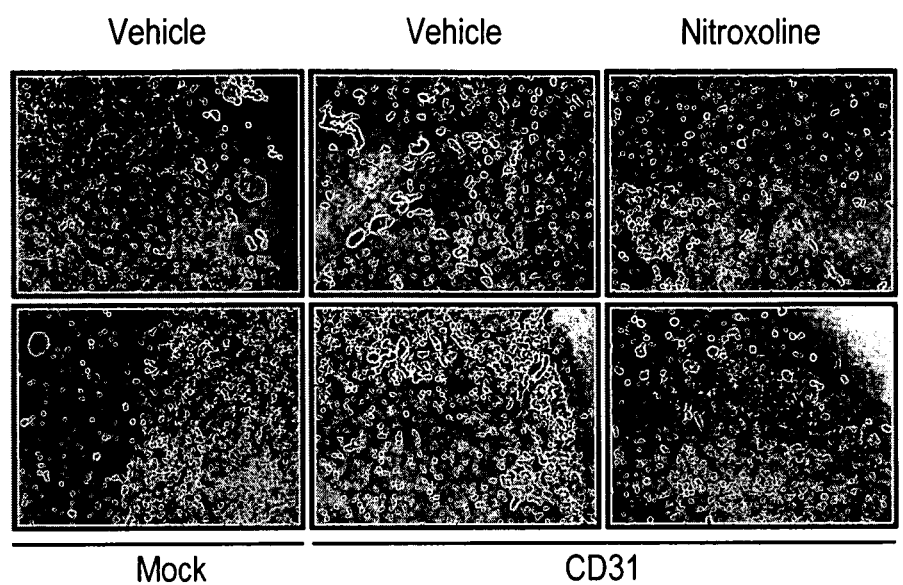
Figure 9E:
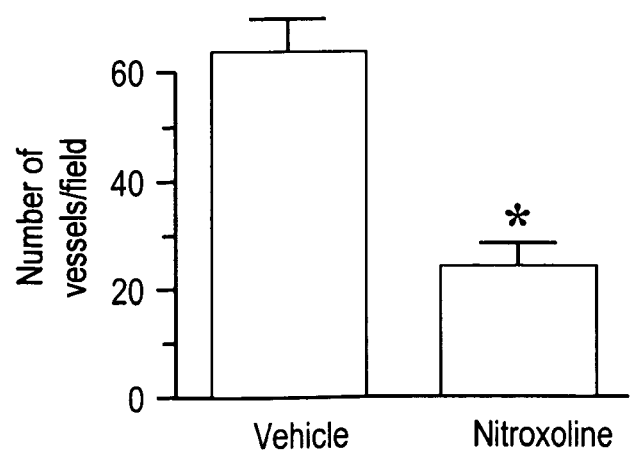

Having observed a clear inhibitory effect of nitroxoline on angiogenesis both in vitro and in vivo, its effect on the growth of breast cancer in a mouse xenograft model was examined. HCC1954 breast cancer cells were subcutaneously transplanted into nude mice and the animals were treated with either vehicle or nitroxoline every other day via i.p. injection for a total 30 days. Nitroxoline significantly blocked the growth of HCC1954 xenografts starting on day 15 with a 55% inhibition at day 30 (FIGS. 9A and B). To see if nitroxoline affect SirT1 activity in vivo, the protein level and the acetylation status of p53 in the tumor tissues were analyzed. As shown in FIG. 9C, nitroxoline significantly induced p53 acetylation in all the representative tumor tissues. The level of p53 protein was also increased by nitroxoline, suggesting that nitroxoline inhibited SirT1 and MetAP2 activity in vivo. To assess whether inhibition of tumor growth is accompanied by inhibition of angiogenesis, we performed immunohistochemical staining of tumor tissues using anti-CD31 antibodies, a marker for new blood vessels. Nitroxoline strongly inhibited tumor-associated angiogenesis, indicating that it is capable of blocking tumor-induced angiogenesis in vivo (FIGS. 9D and E).

V. Pharmaceutical Compositions/Methods of Administration

In one aspect, the invention provides a composition comprising a compound of the invention and an additional therapeutic agent. In one embodiment, the additional therapeutic agent is a methionine aminopeptidase-inhibiting compound. In one embodiment, the additional therapeutic agent is an angiogenesis-inhibiting compound. In another embodiment, the additional therapeutic agent is an anticancer compound.

In another aspect, the invention provides a pharmaceutical composition comprising a compound of the invention and a pharmaceutically suitable excipient.

The present invention is also directed to pharmaceutical compositions comprising an effective amount of one or more compounds according to the present invention (including a pharmaceutically acceptable salt, thereof), optionally in combination with a pharmaceutically acceptable carrier, excipient or additive.

A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

The compounds of the present invention may be administered orally, parenterally, by inhalation spray, rectally, vaginally, or topically in dosage unit formulations containing conventional pharmaceutically acceptable carriers, adjuvants, and vehicles. The term parenteral as used herein includes, subcutaneous, intravenous, intramuscular, intrasternal, infusion techniques, intraperitoneally, eye or ocular, intrabuccal, transdermal, intranasal, into the brain, including intracranial and intradural, into the joints, including ankles, knees, hips, shoulders, elbows, wrists, directly into tumors, and the like, and in suppository form.

The pharmaceutically active compounds of this invention can be processed in accordance with conventional methods of pharmacy to produce medicinal agents for administration to patients, including humans and other mammals.

Modifications of the active compound can affect the solubility, bioavailability and rate of metabolism of the active species, thus providing control over the delivery of the active species. Further, the modifications can affect the anti-angiogenesis activity of the compound, in some cases increasing the activity over the parent compound. This can easily be assessed by preparing the derivative and testing its activity according to known methods well within the routineer's skill in the art.

Pharmaceutical compositions based upon these chemical compounds comprise the above-described compounds in a therapeutically effective amount for treating diseases and conditions which have been described herein, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regimen to be employed, the pharmacokinetics of the agent used, as well as the patient (animal or human) treated.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used.

The active compound is included in the pharmaceutically acceptable carrier or diluent in an amount sufficient to deliver to a patient a therapeutically effective amount for the desired indication, without causing serious toxic effects in the patient treated.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material—of the above type, a liquid carrier such as a fatty oil. In addition, dosage unit forms can contain various other materials which modify the physical form of the dosage unit, for example, coatings of sugar, shellac, or enteric agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Methods of formulating such slow or controlled release compositions of pharmaceutically active ingredients, are known in the art and described in several issued US Patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

A skilled artisan will recognize that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

The compound may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

It should be understood that in addition to the ingredients particularly mentioned above, the formulations of the present invention may include other agents conventional in the art having regard to the type of formulation in question, for example, those suitable for oral administration may include flavoring agents.

In certain pharmaceutical dosage forms, the pro-drug form of the compounds may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development*; 2 ed.; Overseas Publ.: Amsterdam, 1996; pp 351-385; Pitman, I. H. *Medicinal Research Reviews* 1981, 1, 189-214. The prodrug forms may be active themselves, or may be those such that when metabolized after administration provide the active therapeutic agent in vivo.

Pharmaceutically acceptable salt forms may be the preferred chemical form of compounds according to the present invention for inclusion in pharmaceutical compositions according to the present invention.

Certain of the compounds, in pharmaceutical dosage form, may be used as agents for preventing a disease or condition from manifesting itself. In certain pharmaceutical dosage forms, the pro-drug form of the compounds according to the present invention may be preferred. In particular, prodrug forms which rely on $C_1$ to $C_{20}$ ester groups or amide groups (preferably a hydroxyl, free amine or substituted nitrogen group) which may be transformed into, for example, an amide or other group may be particularly useful in this context.

The present compounds or their derivatives, including pro-drug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

Preferred unit dosage formulations are those containing a daily dose or unit, daily sub-dose, as hereinabove recited, or an appropriate fraction thereof, of the administered ingredient.

The dosage regimen for treating a disorder or a disease with the hMetAP-inhibiting compounds or angiogenesis inhibiting compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject will depend on a number of factors, such as the mode of administration, the nature of the condition being treated, the body weight of the subject being treated and the judgment of the prescribing physician.

The amount of compound included within therapeutically active formulations according to the present invention is an effective amount for treating the infection or condition. In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg/day to about 100 mg/kg/day. The dosage of the compound will depend on the condition being treated, the particular compound, and other clinical factors such as weight and condition of the patient and the route of administration of the compound. It is to be understood that the present invention has application for both human and veterinary use.

The compound is conveniently administered in any suitable unit dosage form, including but not limited to one containing 1 to 3000 mg, preferably 5 to 500 mg of active ingredient per unit dosage form. An oral dosage of 10-250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In certain embodiments, the compound is administered once daily; in other embodiments, the compound is administered twice daily; in yet other embodiments, the compound is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compounds of the invention can be used to treat diseases and disease conditions that are acute, and may also be used for treatment of chronic conditions. In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

In one aspect, the invention provides a pharmaceutical composition comprising a compound of formula I and a pharmaceutically suitable excipient.

Still other objects, features, and attendant advantages of the present invention will become apparent to those skilled in the art from a reading of the preceding detailed description of embodiments constructed in accordance therewith, taken in conjunction with any accompanying drawings.

The invention will be further described in the following examples. It should be understood that these examples are for illustrative purposes only and are not to be construed as limiting this invention in any manner.

EXAMPLES

General Methods.

Thin-layer chromatography was performed Merck pre-coated silica gel 60 F-254 plates and were visualized using 254 nm UV light, or by staining with iodine, ceric ammonium molybdate stain. Silica gel (200-400 mesh, Merck) was used for air-flashed chromatography. Reagents were purchased from Aldrich, Acros, or Lancaster companies. Melting points were recorded on a Mel-Temp II apparatus and are uncorrected. NMR data were collected on a Varian Unity-400 (400 MHz $^1$H, 100.6 MHz $^{13}$C) machine at the Department of Pharmacology and Molecular Sciences, The Johns Hopkins University. $^1$H NMR spectra were obtained in deuteriochloroform (CDCl$_3$) with tetramethylsilane (TMS, δ=0.00 for $^1$H) or chloroform (δ=7.26 for $^1$H), or acetone-d$_6$ with TMS or acetone (δ=2.05 for $^1$H) as an internal reference. $^{13}$C NMR spectra were proton decoupled and were either in CDCl$_3$ with either TMS (δ=0.0 for $^{13}$C) or chloroform (δ=77.0 for $^{13}$C), or acetone-d$_6$ with TMS or acetone (δ=0.0 for $^{13}$C) as an internal reference. Chemical shifts are reported in ppm (δ); multiplicities are indicated by s (singlet), d (doublet), t (triplet), q (quartet), m (multiplet), dd (doublet of doublet), dt (doublet of triplet), br. (broad), app. (apparent) and exch. (exchangeable); coupling constants, J, are reported in Hertz (Hz); integration is provided; assignments of individual resonances are supported in most cases by the following NMR experiments: APT/DEPT, COSY, or HMBC and HMQC. Data are presented in the form: chemical shift (multiplicity, coupling constants, integration and assignments where relevant). Low-resolution mass spectra were obtained on a Voyager DE-STR, MALDI-TOF instrument at the AB Mass Spectrometry/Proteomics Facility at the Johns Hopkins University. The MALDI-samples were prepared by mixing droplets of the sample solutions in chloroform or methanol and 2,5-dihydroxybenzoic acid solution in acetone, where the latter served as the matrix. Data are reported in the form m/z (intensity relative to base=100). The solvents used in reactions were reagent grade. The solvents used for extraction and chromatography were technical grade. The quinolinol 1e and carbamate 4a were acquired from ASDI Inc., Delaware. All nonaqueous reactions were performed in oven-dried glassware.

Example 1

General Procedure for the Synthesis of 7-(2-aminomethyl)-8-hydroxy-quinolines

The Mannich bases 2a through 2g were prepared by modifying a known procedure.

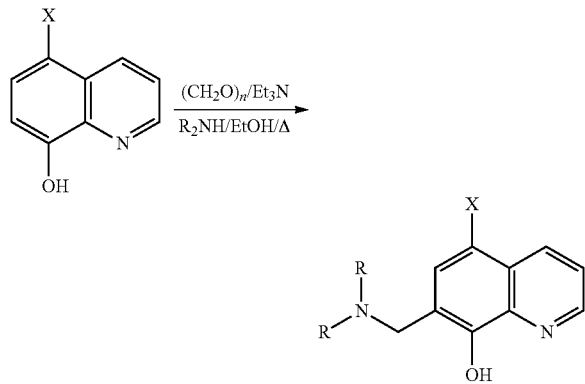

To a solution of 8-hydroxyquinoline (1 mmol) in absolute ethanol (15 mL); triethylamine (1.2 mmol) and paraformaldehyde (1.2 mmol, 36.2 mg) were added and the reaction mixture was refluxed for 12 h and cooled to room temperature. The reaction mixture was filtered and the filtrate was concentrated. Recrystallization of the residue from 1:1 EtOH—$H_2O$ was the way of purification unless stated otherwise.

5-Chloro-7-(N,N-bis(2-hydroxyethyl)aminomethyl)-8-hydroxy-quinoline (2a)

The crude product obtained after evaporating the solvent from the reaction mixture was subjected to flash-column chromatography over silica gel while eluting with dichloromethane and pure 2a was thus produced as an amber-colored syrup (213 mg, 72%).
Analytical Data for 2a:
$R_f$ 0.12 (7:3 hexanes-EtOAc)
$^1$H NMR (400 MHz, $CDCl_3$) δ: 8.84 (dd, J=4.4, 1.3 Hz, 1H, H-2), 8.62 (dd, J=5.5, 1.3 Hz, 1H, H-4), 8.12 (dd, J: 5.5, 4.4 Hz, 1H, H-3), 7.54 (d, J: 5.8 Hz, 1H, H-7),
7.18 (d, J=5.8 Hz, 1H, H-6), 4.02 (br t, J=6.7 Hz, 4H, —$CH_2$—OH), 3.86 (s, 2H, —$CH_2$-7), 3.12 (br s exch., 3H, —$CH_2$—OH, 8-OH), 3.05 (br t, J=6.8 Hz, 4H, —N—$CH_2$—)
MS (MALDI-TOF) m/z: 296 (100)

5-Chloro-7-((N-piperidino)methyl)-8-hydroxy-quinoline (2b)

Yield: 265 mg, 96%
Analytical Data for 2b:
$R_f$ 0.35 (7:3 hexanes-EtOAc)
mp 92° C.
$^1$H NMR (400 MHz, $CDCl_3$) δ: 8.98 (dd, J=4.4, 1.0 Hz, 1H, H-2), 8.51 (dd, J=5.6, 1.1 Hz, 1H, H-4), 7.55 (dd, J=5.6, 4.4 Hz, 1H, H-3), 7.28 (s, 1H, H-6), 3.82 (s, 2H, $CH_2$-7), 2.63 (br s, 5H, 2',6'-piperidine, OH), 1.72 (m, 4H, 3',5'-piperidine), 1.44 (br s, 2H, 4'-piperidine)
MS (MALDI-TOF) m/z: 277 (100)

7-((N-morpholino)methyl)-8-hydroxy-quinoline (2c)

Yield: 230 mg, 94%
Analytical Data for 2c:
$R_f$ 0.30 (7:3 hexanes-EtOAc)
mp 66° C.
$^1$H NMR (400 MHz, $CDCl_3$) δ: 8.94 (dd, J=3.3, 1.1 Hz, 1H, H-2), 8.59 (dd, J=4.6, 1.1 Hz, 1H, H-4), 8.12 (dd, J=4.6, 1.2 Hz, 1H, II-5), 7.41 (m, 2H, H-3, H-6), 3.82 (s, 2H, $CH_2$-7), 3.78 (m, 4H, 2,6-morpholine), 2.62 (br s, 4H, 3,5-morpholine), 1.31 (br s exch., 1H, OH)
MS (MALDI-TOF) m/z: 245

5-Chloro-7-((N-morpholino)methyl)-8-hydroxy-quinoline (2d)

Yield: 253 mg, 91%
Analytical Data for 2d:
$R_f$ 0.32 (7:3 hexanes-EtOAc)
mp 128° C.
$^1$H NMR (400 MHz, $CDCl_3$) δ: 8.93 (dd, J=3.4, 1.1 Hz, 1H, H-2), 8.52 (dd, J=4.5, 1.1 Hz, 1H, H-4), 7.57 (dd, J=4.5, 3.4 Hz, 1H, H-3), 7.41 (s, 1H, H-6), 3.84 (s, 2H, $CH_2$-7), 3.79 (m, 4H, 2,6-morpholine), 2.63 (br s, 4H, 3,5-morpholine), 1.30 (br s exch., 1H, OH)
MS (MALDI-TOF) m/z: 279

5-Chloro-7-(1-(4-methylpiperazino)methyl)-8-hydroxy-quinoline (2e)

Yield: 244 mg, 83%
Analytical Data for 2e:
$R_f$ 0.18 (7:3 hexanes-EtOAc)
ms 134° C.
$^1$H NMR (400 MHz, acetone-$d_6$) δ: 8.90 (dd, J=4.0, 1.2 Hz, 1H, H-2), 8.52 (dd, J=8.4, 1.6 Hz, 1H, H-4), 7.68 (dd, J=8.6, 4.2 Hz, 1H, H-3), 7.64 (s, 1H, H-6), 3.81 (s, 2H, $CH_2$-7), 2.84 (br s exch., OH), 2.57 (br s, 4H, piperazine), 2.41 (br s, 4H, piperazine), 2.21 (s, 3H, N—$CH_3$)
MS (MALDI-TOF) m/z: 292

Example 2

General Procedure for the Synthesis of 7-(2-amino-2-arylmethyl)-8-hydroxy-quinolines

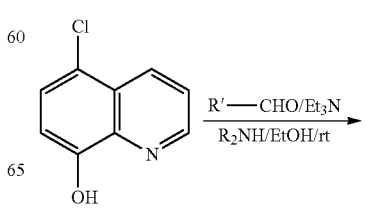

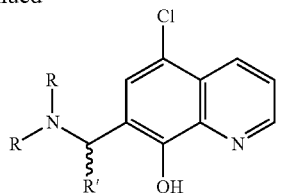

To a solution of 5-chloro-8-hydroxyquinoline (1 mmol, 180 mg) in absolute ethanol (15 mL); triethylamine (1 mmol) and aromatic aldehyde (1 mmol) were added and the reaction mixture was stirred at room temperature for 2 days. The reaction mixture was was concentrated and the residue was recrystallized from 1:1 EtOH—H$_2$O.

5-Chloro-7-(1-phenyl-1-(N-morpholino)-methyl)-8-hydroxy-quinoline (2f)

Yield: 315 mg, 89%

Analytical Data for 2f:

$R_f$ 0.35 (7:3 hexanes-EtOAc)

mp 89° C.

$^1$H NMR (400 MHz, acetone-d$_6$) δ: 8.91 (pair of dds, J=3.4, 1.2 Hz, 1H, H-2), 8.53 (pair of dds, J=6.5, 1.4 Hz, 1H, H-4), 7.71 (pair of dds, J=6.5, 4.4 Hz, 1H, H-3), 7.61 (pair of ds, J=8.0 Hz, 2H, 2,6-Ph), 7.27 (pair of ts, J=8.0 Hz, 2H, 3,5-Ph), 7.15 (d, 1H, 4-Ph), 3.71 (br t, J=4.8 Hz, 2H, 2,6-morpholine), 2.88 (br s, 3H, 2,6-morpholine, OH), 2.85 (br s, 1H, —N—CH(Ph)-), 2.47 (br s, 4H, 3,5-morpholine)

$^{13}$C NMR (100 MHz, acetone-d$_6$) δ: 153.35, 150.43, 149.97, 149.87, 142.38, 139.99, 133.73, 133.54 (C-4), 129.56 & 128.97 (3,5-Ph), 128.54 & 128.20 (2,6-Ph), 127.26 (4-Ph), 125.92, 125.42, 124.00 (C-3), 123.69 (C-2), 120.86, 111.28, 69.09 & 67.55 (2,6-morpholine), 53.51 (3,5-mopholine) 355 (95)

5-Chloro-7-(1-(2-furyl)-1-(2-thiazolylamino)-methyl)-8-hydroxy-quinoline (2g)

Yield: 258 mg, 72%

Analytical Data for 2g:

$R_f$ 0.32 (7:3 hexanes-EtOAc)

mp 126° C.

$^1$H NMR (400 MHz, CDCl$_3$) δ: 8.85 (dd, J=4.0, 1.6 Hz, 1H, H-2), 8.51 (dd, J=8.4, 1.6 Hz, 1H, H-4), 7.69 (s, 1H, H-6), 7.57 (dd, J=8.4, 4.4 Hz, 1H, H-3), 7.41 (dd, J=2.8, 0.8 Hz, 1H, furyl-H5), 7.15 (d, J=3.6 Hz, 1H, thiazole-H5), 6.55 (d, J=3.6 Hz, 1H, thiazole-H4), 6.40 (s exch., 1H, —OH), 6.34 (dd, J=3.2, 2.0 Hz, 1H, furyl-H3), 6.27 (dd, J=2.8, 0.8 Hz, 1H, furyl-H4), 1.62 (br s, 1H, —NH—)

$^{13}$C NMR (100 MHz, CDCl$_3$) δ: 168.93, 152.62, 149.11, 148.72, 142.47, 138.84, 138.60, 133.13, 126.32, 125.85, 122.53, 121.55, 120.61, 110.42, 107.74, 107.11, 52.02

MS (MALDI-TOF) m/z: 358 (98)

Example 3

Synthesis of 8-Allyloxy-5-chloroquinoline (3a)

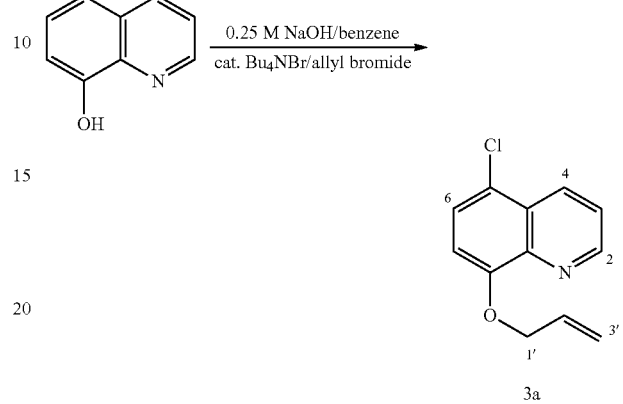

A solution of 5-chloro-8-hydroxyquinoline (1 mmol, 180 mg) in aqueous NaOH (0.25 M, 8 mL; 2 mmol) containing tetrabutylammonium bromide as the phase-transfer catalyst (0.1 mmol, 33 mg) was stirred for 30 min., and allyl bromide (1 mmol, 85 µL) and benzene (8 mL) were added and the reaction mixture was stirred vigorously at 50° C. for 14 h. The reaction mixture was partitioned between water (15 mL) and EtOAc (15 mL) after cooling to room temperature and the extraction was repeated twice. The organic layers were combined and washed with 1 M NaOH solution (15 mL) and concentrated. The crude product was purified by flash-column chromatography over silica gel using 1:2 hexanes-ether as eluent to afford quinoline 3a as a light-brown solid (170 mg, 64%).

Analytical Data for 3a:

$R_f$ 0.55 (7:3 hexanes-EtOAc)

mp 49° C.

$^1$H NMR (400 MHz, CDCl$_3$) δ: 9.04 (dd, J=4.4, 1.3 Hz, 1H, H-2), 8.58 (dd, J=5.5, 1.3 Hz, 1H, H-4), 7.56 (dd, J: 5.5, 4.4 Hz, 1H, H-3), 7.54 (d, J: 5.8 Hz, 1H, H-7), 6.99 (d, J=5.8 Hz, 1H, H-6), 6.31-6.18 (m, 1H, H-2'), 5.48 (dt, J=15.2, 3.4 Hz, 1H, H-3') 5.37 (dt, J=9.4, 3.4 Hz, 1H, H-3"), 4.88 (m, 2H, H-1')

$^{13}$C NMR (100 MHz, CDCl$_3$) δ: 149.79, 143.67, 132.92, 132.68, 131.23, 126.27, 125.87, 122.30, 121.98, 118.64, 109.07, 69.94 (C-1')

MS (MALDI-TOF) m/z: 220

Synthesis of 8-(2-hydroxyethyl)5-chloroquinoline (3b)

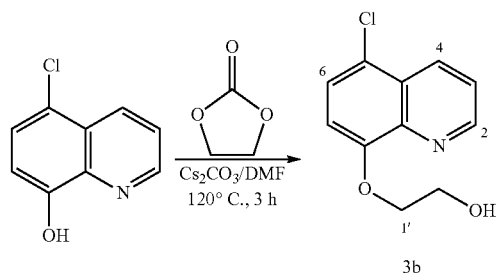

A mixture of 5-chloro-8-hydroxyquinoline (1 mmol, 180 mg), ethylene carbonate (2 mmol, 180 mg) and $Cs_2CO_3$ (0.6 mmol, 195 mg) in dry DMF (10 mL) was stirred vigorously at 120° C. for 3 h. DMF was evaporated under high-vacuum and the residue was dissolved in water (15 mL), extracted twice with dichloromethane (15 mL), and the residue left after evaporation of dichloromethane was chromatographed over silica gel (eluent: 4:1 hexanes-EtOAc). A biege colored solid was obtained (174 mg, 78%).

Analytical Data for 3b:

$R_f$ 0.32 (7:3 hexanes-EtOAc)

mp 72° C.

$^1$H NMR (400 MHz, acetone-$d_6$) δ: 8.97 (dd, J=3.4, 1.6 Hz, 1H, H-2), 8.58 (dd, J=8.0, 1.6 Hz, 1H, H-4), 7.73 (dd, J=8.8, 4.4 Hz, 1H, H-3), 7.66 (d, J=8.4 Hz, 1H, H-7), 7.26 (d, J=8.4 Hz, 1H, H-6), 4.96 (br. s, exch. 1H, OH), 4.28 (t, J=4.8 Hz, 2H, H-1'), 3.99 (br. s, 2H, H-2')

MS (MALDI-TOF) m/z: 224

Example 4

General Procedure for the Synthesis of 8-Quinolyl Carbamates

Triethylamine (3 drops) was added to a suspension of 8-hydroxyquinoline (1 mmol) and an isocyanate (1 mmol) in diethyl ether (15 mL). The reaction mixture was stirred for 2 days at room temperature and the solvent was removed using a rotary evaporator and the residue was subjected to flash-column chromatography over silica gel (eluent: hexanes or 5% EtOAc in hexanes) to afford the respective quinolyl carbamate.

5,7-Dichloro-8-quinolyl-N-(3,5-dichlorophenyl)-carbamate (4b)

Yield: 233 mg, 58%

Analytical Data for 4b:

$R_f$ 0.64 (7:3 hexanes-EtOAc)

mp 148° C.

$^1$H NMR (400 MHz, $CDCl_3$) δ: 10.56 (br s, 1H, NH); 8.68 (dd, J=4.4, 1.6 Hz, 1H, H-2); 8.52 (dd, J=8.8, 1.5 Hz, 1H, H-4); 7.62 (s, 1H, H-6); 7.59 (dd, J=8.8, 4.4 Hz, 1H, H-3); 7.12 (app. t, J=2.0 Hz, 2H, 2,6-aniline); 7.18 (d, J=2.0 Hz, 1H, 4-aniline)

$^{13}$C NMR (100 MHz, $CDCl_3$) δ: 154.62, 152.44, 149.81, 140.74, 136.15, 135.53, 132.78, 131.33, 128.56, 126.27, 122.30, 121.98, 121.87, 118.52

MS (MALDI-TOF) m/z: 403

5-Chloro-8-quinolyl-N-(3,5-dichlorophenyl)-carbamate (4c)

Yield: 300 mg, 82%

Analytical Data for 4c:

$R_f$ 0.61 (7:3 hexanes-EtOAc)

mp 159° C.

$^1$H NMR (400 MHz, Acetone-$d_6$) δ: 9.88 (br s, 1H, NH), 8.99 (dd, J=4.4, 1.6 Hz, 1H, H-2), 8.65 (dd, J=8.6, 1.4 Hz, 1H, H-4), 7.81 (d, J=8.2 Hz, 1H, H-7), 7.75 (dd, J=8.6, 3.8 Hz, 1H, H-3), 7.70 (app. t, J=2.0 Hz, 2H, H-2,6-aniline), 7.65 (d, J=8.2 Hz, 1H, H-6), 7.20 (app. t, J=2.0 Hz, H-4-aniline)

$^{13}$C NMR (100 MHz, Acetone-$d_6$) δ: 152.13, 143.35, 142.40, 135.91, 133.61, 128.96, 127.88, 127.34, 124.02, 123.46, 122.85, 117.63

MS (MALDI-TOF) m/z: 367

5,7-Dichloro-8-quinolyl-N-phenylcarbamate (4d)

Yield: 253 mg, 76%

Analytical Data for 4d:

$R_f$ 0.66 (7:3 hexanes-EtOAc)

mp 136° C.

$^1$H NMR (400 MHz, $CDCl_3$) δ: 8.98 (dd, J=4.3, 1.2 Hz, 1H, H-2), 8.59 (dd, J=5.8, 1.2 Hz, 1H, H-4), 7.73 (s, 1H, H-6), 7.58 (dd, J=5.5, 3.4 Hz, 1H, H-3), 7.51 (app. d, J=6.1 Hz, 2H, H-2,6-aniline), 7.44 (br s, 1H, NH), 7.37 (t, J=6.2 Hz, 2H, H-3,5-aniline), 7.16 (t, J=6.2 Hz, 1H, H-4-aniline)

MS (MALDI-TOF) m/z: 333

5-Chloro-8-quinolyl-N-phenylcarbamate (4e)

Yield: 257 mg, 86%

Analytical Data for 4e:

$R_f$ 0.65 (7:3 hexanes-EtOAc)

mp 129° C.

$^1$H NMR (400 MHz, $CDCl_3$) δ: 9.01 (dd, J=4.3, 1.2 Hz, 1H, H-2), 8.59 (dd, J=5.8, 1.2 Hz, 1H, H-4), 7.76 (br s, 1H, NH), 7.63 (d, J=5.9 Hz, 1H, H-7), 7.58 (m, 2H, H-2,6-aniline), 7.54 (d, J=5.9 Hz, 1H, H-6), 7.26 (t, J=6.2 Hz, 1H-3,5-aniline), 7.13 (t, J=6.2 Hz, 1H, H-4-aniline)

MS (MALDI-TOF) m/z: 299

5,7-Dichloro-8-quinolyl-N-(4-fluorophenyl)-carbamate (4f)

Yield: 312 mg, 89%

Analytical Data for 4f:

$R_f$ 0.68 (7:3 hexanes-EtOAc)

mp 148° C.

$^1$H NMR (400 MHz, $CDCl_3$) δ: 8.85 (br s, 1H, NH), 7.71 (dd, J=5.1, 3.3 Hz, 1H, H-2), 7.53 (dd, J=5.7, 3.5 Hz, 1H, H-4), 7.43 (dd, J=8.8, 4.8 Hz, 1H, H-3), 7.35 (s, 1H, H-6), 7.28 (t, J=8.3 Hz, 2H, H-2,6-aniline), 7.01 (t, J=8.8, 2H, H-3,5-aniline)

$^{13}$C NMR (100 MHz, $CDCl_3$) δ: 161.14 (d), 149.05, 133.93, 131.99, 131.90, 131.16, 129.07, 122.90, 122.82, 118.03, 117.98, 116.12, 115.90

MS (MALDI-TOF) m/z: 351

5-Chloro-8-quinolyl-N-(3,5-difluorophenyl)-carbamate (4g)

Yield: 188 mg, 56%

Analytical Data for 4g:

$R_f$ 0.67 (7:3 hexanes-EtOAc)

mp 152° C.

$^1$H NMR (400 MHz, $CDCl_3$) δ: 8.98 (dd, J=4.4, 1.3 Hz, 1H, H-2); 8.56 (dd, J=5.5, 1.3 Hz, 1H, H-4); 8.32 (br s, 1H, NH); 7.59 (dd, J=5.5, 4.4 Hz, 1H, H-3); 7.53 (d, J=5.8 Hz, 1H, H-7); 7.41 (d, J=6.3 Hz, 2,6-aniline); 7.01 (d, J=5.8 Hz, 1H, H-6); 6.42 (d, J=6.3 Hz, 1H, 4-aniline)

$^{13}$C NMR (100 MHz, $CDCl_3$) δ: 165.01 (d), 153.11, 151.23, 150.89, 140.31, 139.46, 132.92, 128.45, 126.27, 122.30, 121.98, 112.47, 109.07 & 108.78 (pair of ds), 103.02 (t)

MS (MALDI-TOF) m/z: 335

5-Chloro-8-quinolyl-N-(2-chloroethyl)-carbamate (4h)

Yield: 248 mg, 87%
Analytical Data for 4h:
$R_f$ 0.54 (7:3 hexanes-EtOAc)
mp 138° C.
$^1$H NMR (400 MHz, acetone-$d_6$) δ: 8.92 (d, J=2.8 Hz, 1H, H-2), 8.62 (d, J=8.8 Hz, 1H, H-4), 7.77-7.69 (m, 2H, H-6,7), 7.54 (d, J=8.4 Hz, 1H, H-3), 7.37 (br s, 1H, NH),
3.76 (t, J=6.4 Hz, 2H, H-2'), 3.59 (apparent q, J=6 Hz, 2H, H-1')
$^{13}$C NMR (100 MHz, acetone-$d_6$) δ: 155.02, 151.75, 151.72, 143.61, 128.20, 127.99, 133.50, 127.28, 123.79, 122.69, 44.08, 43.82
MS (MALDI-TOF) m/z: 285

5,7-Dichloro-8-quinolyl-N-(2-chloroethyl)-carbamate (4i)

Yield: 233 mg, 73%
Analytical Data for 4i:
$R_f$ 0.65 (7:3 hexanes-EtOAc)
mp 112° C.
$^1$H NMR (400 MHz, acetone-$d_6$) δ: 9.00 (dd, J=4.0, 1.2 Hz, 1H, H-2), 8.60 (dd, J=8.4, 1.1 Hz, 1H, H-4), 7.88 (s, 1H, H-6), 7.75 (dd, J=8.4, 4.0 Hz, 1H, H-3), 7.54 (br s, 1H, NH), 3.76 (t, J=6 Hz, 2H, H-2'), 3.61 (app. q, J=6 Hz, 2H, H-1')
$^{13}$C NMR (100 MHz, acetone-$d_6$) δ: 154.29, 152.90, 150.87, 139.78, 133.98, 133.61, 129.00, 127.97, 126.62, 124.08, 44.16, 43.72
MS (MALDI-TOF) m/z: 319

Example 5

2-Methyl-5,7-dinitro-8-hydroxy-quinoline (5b)

Quinaldine (6.3 mmol, 1 g) was added slowly in small portions to a mixture of concentrated $HNO_3/H_2SO_4$ (10 mL) in an ice-bath, and after 2 h, the mixture was poured on crushed-ice. A yellow powder was filtered, washed with hot EtOH, and crystallized from nitrobenzene.
Yield: 1.1 g, 69%
mp 260° C. (decomposes)
$^1$H NMR (400 MHz, DMSO-$d_6$) δ: 12.03 (s, 1H, OH), 9.66 (d, $J_{3,4}$=8.8 Hz, 1H, H-4), 9.21 (s, 1H, H-6), 8.15 (d, $J_{3,4}$=8.8 Hz, 1H, H-3), 2.94 (s, 3H, Me).
MS (MALDI-TOF) m/z: 242, 249 ($M^+$)

5-Nitro-8-tert-butoxycarbonyloxyquinoline (5c)

DMAP (122 mg, 1.0 mmol) and DIPEA (2 mL, 12 mmol) were added at room temperature to a stirred suspension of nitroxoline (1.9 g, 10 mmol) and di-tert-butyl dicarbonate (2.2 g, 10 mmol) in a 1:2 mixture of hexanes-DCM (80 mL). The mixture was stirred for 14 hours at room temperature, filtered using paper filter and the filtrate was concentrated in vacuum to provide a crude product as yellowish oil. The product was purified by flash column chromatography on silica gel (eluent: Hexanes/DCM=7:3).
Yield: 2.7 g, 92%
$R_f$ 0.65 (2:3 EtOAc/hexanes)
$^1$H NMR (400 MHz, CDCl$_3$) δ: 8.89 (d, J=8.8 Hz, 1H, H-4), 8.91 (d, J=3.6 Hz, 1H, H-2), 8.35 (d, J=8.4 Hz, 1H, H-6), 7.57 (dd, J=8.8 Hz & 3.6 Hz, 1H, H-3), 7.45 (d, J=8.8 Hz, 1H, H-7), 1.52 (s, 9H, t-Bu).
$^{13}$C NMR (100 MHz, CDCl$_3$) δ: 153.7, 152.1, 151.4, 142.9, 141.12, 132.4, 125.5, 124.6, 122.8, 119.9, 84.1, 27.6.
MS (MALDI-TOF) m/z: 296 (M−16+23), 291 (MH$^+$), 266, 249, 233 (M−Bu−t)

Ethyl 1-(5-Nitro-quinolin-8-yloxy)-acetate (5d)

Nitroxoline (1 g, 5.3 mmol) was heated at 60° C. with ethyl bromoacetate (0.6 mL, 5.3 mmol) and potassium carbonate (1 g, 7.3 mmol) in DMSO for 18 h, cooled to rt, diluted with water (30 mL) and extracted with a mixture of 2:3 EtOAc/Et$_2$O. Solvent was evaporated and the crude product was purified by column chromatography on silica gel (eluent: 1:3 EtOAc/DCM).
Yield: 980 mg, 67%
$R_f$ 0.38 (2:3 EtOAc/hexanes)
$^1$H NMR (400 MHz, CDCl$_3$) δ: 9.15 (d, J=8.8 Hz, 1H, H-4), 9.01 (d, J=3.5 Hz, 1H, H-2), 8.42 (d, J=8.8 Hz, 1H, H-6), 7.67 (dd, J=8.8 Hz & 3.5 Hz, 1H, H-3), 6.93 (d, J=8.8 Hz, 1H, H-7), 5.03 (s, 2H, O—CH$_2$—CO), 4.25 (q, J=7.5 Hz, 2H, Et), 1.25 (t, J=7.6 Hz, 3H, Et).
MS (MALDI-TOF) m/z: 277 (MH$^+$), 299 (M+Na$^+$)

1-(5-Nitro-quinolin-8-yloxy)-acetamide (5e)

Acetamide 5e was also prepared according to the procedure described above for making the acetate 5d, except the reaction was run at 1 mmol scale, and potassium carbonate was supplanted with cesium carbonate.
Yield: 193 mg, 78%
Analytical Data for 5e
$R_f$ 0.31 (2:3 EtOAc/hexanes)
$^1$H NMR (400 MHz, CDCl$_3$) δ: 9.4 (d, J=8.8 Hz, 1H, H-4), 8.81 (d, J=3.5 Hz, 1H, H-2), 8.55 (d, J=8.8 Hz, 1H, H-6), 7.68 (dd, J=8.8 Hz & 3.5 Hz, 1H, H-3), 7.51 (d, J=8.8 Hz, 1H, H-7), 6.8 (br s, 2H, NH$_2$), 4.2 (s, 2H, O—CH$_2$—CO).
MS (MALDI-TOF) m/z: 248 (MH$^+$), 270 (M+Na$^+$)

Synthesis of 5-Nitro-quinolin-8-yl pivaolate (5f)

Pivaloyl chloride (250 μL, 2 mmol) was added to a mixture of nitroxoline (380 mg, 2 mmol), DMAP (98 mg, 0.8 mmol), and Et$_3$N (1.1 mL, 8 mmol) in DCM (20 mL) at rt, and the mixture was stirred vigorously for 14 h. The reaction mixture was washed with 10% aqueous NaHCO$_3$ and the DCM layer was concentrated. The crude residue was subjected to flash column chromatography (eluent: Hexanes/DCM=7:3) to afford pivolate 5 g as a yellow solid.

Yield: 465 mg, 85%

$R_f$ 0.67 (2:3 EtOAc/hexanes)

$^1$H NMR (400 MHz, CDCl$_3$) δ: 8.99 (d, J=8.8 Hz, 1H, H-4), 8.93 (d, J=3.6 Hz, 1H, H-2), 8.38 (d, J=8.4 Hz, 1H, H-6), 7.59 (dd, J=8.8 Hz & 3.6 Hz, 1H, H-3), 7.46 (d, J=8.8 Hz, 1H, H-7), 1.49 (s, 9H, t-Bu).

$^{13}$C NMR (100 MHz, CDCl$_3$) δ: 176.99, 153.69, 151.44, 142.92, 141.22, 132.39, 125.54, 124.62, 122.82, 119.95, 39.71, 27.58.

MS (MALDI-TOF) m/z: 295 (M+Na$^+$), 249.

The compounds of the invention and relevant biological data be found in the following tables.

TABLE 2

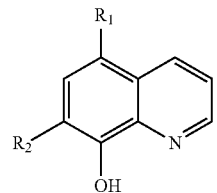

1

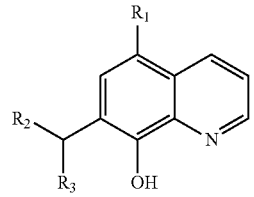

2

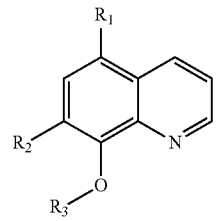

3

| Entry | R$^1$ | R$^2$ | R$^3$ | hMetAP2 Mn$^{2+}$ | hMetAP2 Co$^{2+}$ | hMetAP1 Mn$^{2+}$ | hMetAP1 Co$^{2+}$ | Selectivity HUVEC | Selectivity HFF |
|---|---|---|---|---|---|---|---|---|---|
| 1a | H | H | — | 2 | d | d | d | 6.2 | 6.6 |
| 1b | Cl | H | — | 0.18 | d | 12.9 | d | 1.4 | 11.4 |
| 1c | NO$_2$ | H | — | 0.46 | 11.2 | d | d | 1.98 | 13.6 |
| 1d | SO$_3$H | H | — | d | d | d | d | d | d |
| 2a | Cl | H | N(CH$_2$CH$_2$OH)$_2$ | 28 | d | d | d | 10.7 | 0.8 |
| 2b | Cl | H | piperidinyl | 7.7 | d | d | d | 13.5 | 22.6 |
| 2c | H | H | morpholinyl | 15.2 | d | d | d | 33.3 | 9.8 |
| 2d | Cl | H | morpholinyl | 2.7 | d | d | d | 5.6 | 36.3 |
| 2e | Cl | H | (4-methyl)piperazinyl | 3.8 | d | d | d | 9.6 | 15 |
| 2f | Cl | Ph | morpholinyl | 0.33 | 8 | d | 14 | 8.6 | 19.2 |
| 2g | Cl | 2-furyl | 2-thiazolyl | 2.8 | d | d | d | 2.5 | 13.5 |
| 3a | Cl | H | allyl | d | d | d | d | d | d |
| 3b | Cl | H | CH$_2$CH$_2$OH | d | d | d | d | d | d |

All the IC$_{50}$ values are in μM, d = >50 μM

TABLE 3

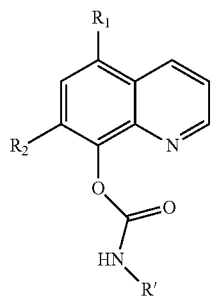

4

| Entry | R¹ | R² | R' | hMetAP2 $Mn^{2+}$ | hMetAP2 $Co^{2+}$ | hMetAP1 $Mn^{2+}$ | hMetAP1 $Co^{2+}$ | Selectivity HUVEC | Selectivity HFF |
|---|---|---|---|---|---|---|---|---|---|
| 4a | Cl | Cl | 2,4,5-trichlorophenyl | 2.6 | d | d | d | 1.3 | 4.9 |
| 4b | Cl | Cl | 2,5-dichlorophenyl | 0.9 | d | d | d | 0.11 | 3 |
| 4c | Cl | H | 2,5-dichlorophenyl | 0.07 | 2.2 | 12.6 | d | 1.2 | 8 |
| 4d | Cl | Cl | Ph | 1.6 | d | d | d | 2.2 | 15.3 |
| 4e | Cl | H | Ph | 0.03 | 1.9 | 11.9 | d | 2.1 | 8.8 |
| 4f | Cl | Cl | 4-fluorophenyl | 3.1 | d | d | d | 2.2 | 37 |
| 4g | Cl | H | 3,5-difluorophenyl | 1.8 | 45.7 | d | >50 | 2.6 | 16.1 |
| 4h | Cl | H | 2-chloroethyl | 0.8 | d | 38.2 | d | 2.3 | 8.4 |
| 4i | Cl | Cl | 2-chloroethyl | 0.3 | d | d | d | 2.4 | 11.1 |

All the $IC_{50}$ values are in μM, d=>50 μM;

TABLE 4

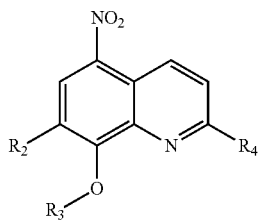

5

| Entry | R⁴ | R² | R³ | hMetAP2 | hMetAP1 | HUVEC |
|---|---|---|---|---|---|---|
| 1c | H | H | H | 0.46 | d | 1.98 |
| 5b | Me | NO₂ | H | | | 17.31 |
| 5c | H | H | CO₂C(Me)₃ | | | 0.29 |
| 5d | H | H | CH₂CO₂Et | | | 7.3 |
| 5e | H | H | CH₂CONH₂ | | | 6.3 |
| 5f | H | H | COC(Me)₃ | | | 1.6 |

All the $IC_{50}$ values are in μM, d=>50 μM; In vitro assays were conducted in the presence of physiologically relevant metal ions (i.e. $Mn^{2+}$ for hMetAP2 and $Co^{2+}$ for hMetAP1)

Example 6

Biological Assays

Cell Culture and Drug Screening

HCC1954 cells were grown in RPMI1640 containing 10% FBS. HUVEC were grown using the EGM-2 bullet kit (Cambrex) as per manufacturer's instructions. The cells were maintained in a humidified incubator adjusted to 5% $CO_2$. For drug screening, 10 mM stock solutions of Johns Hopkins Drug Library were arrayed in 96-well plates and screened at a final concentration of 10 μM. The cell growth was determined using a [³H]-thymidine incorporation assay. Cells (typically 5,000 cells/well) were seeded in 96-well plates containing 0.2 ml of growth media and allowed to adhere for 24 h. The cells were then treated with drugs for 24 h. Cells were pulsed with 1 μCi [³H]-thymidine (MP Biomedicals, 6.7 Ci $mmol^{-1}$) for 8 h and harvested, upon trypsin treatment, onto glass fiber filters (Wallac, Turku, Finland), from which ³H counts were determined using a Perkin Elmer MicroBeta plate reader.

MetAP Enzymatic Assay

Recombinant human MetAP1 and MetAP2 were prepared as previously described (Hu, X. et al (2006) *Proc. Natl. Acad. Sci. U.S.A.* 103, 18148-18153). MetAP enzymes in assay buffer containing 20 mM HEPES, 40 mM KCl, and 10 μM $CoCl_2$ (for MetAP1) or $MnCl_2$ (for MetAP2) were incubated with substrate solution containing 0.6 mM Met-Pro-pNA at room temperature for 20-30 min. The enzyme activity was spectrophotometrically determined by increase in absorbance at 450 nm.

Yeast Growth Assay

*Saccharomyces cerevisiae* strain BY4743 (MATa/α his3Δ1/his3Δ1 leu2Δ0/leu2Δ0 lys2Δ0/LYS2) and its isogenic haploid derivatives for MetAP1 (map1Δ) and MetAP2 (map2Δ) deletion mutants were used for yeast growth assays. Drugs dissolved in DMSO were spotted onto sterile filter disks and dried before experiments. Exponentially growing yeast strains were mixed with top agar and plated on YPD (1% yeast extract/2% peptone/2% glucose) plates. The filter disks were then placed on the YPD plates containing yeasts and the incubation was continued for 48 h at 30° C.

siRNA Construct and Transfection

MetAP2 and SirT1 siRNA oligonucleotides were purchased from Qiagen. HUVECs growing in a 6-well plate were transfected with either MetAP2 or SirT1 siRNA using HiperFect transfection reagent (Qiagen) according to the manufacturer's instruction. After 48 h of transfection, the cells were harvested and analyzed for western blot.

Western Blot

Cells were lysed by adding 1 volume of 2× Laemmli buffer and were then boiled for 5 min. The samples were separated by SDS-PAGE and transferred to nitrocellulose membrane (Bio-Rad). Proteins were detected using primary antibodies for p53 (Santa Cruz), met-14-3-3γ (Novus), p21 (Santa Cruz), Rb (Santa Cruz), MetAP2 (Hu, X. et al (2006) *Proc. Natl. Acad. Sci. U.S.A.* 103, 18148-18153), SirT1 (Santa Cruz), acetyl-p53-K382 (Abcam), acetyl-tubulin (Sigma), histone-H3 (Santa Cruz), acetyl-H3 (Santa Cruz) and α-tubulin (TU-02, Santa Cruz) followed by the incubation with horseradish peroxidase (HRP)-conjugated anti-mouse or anti-rabbit antibodies (Santa Cruz) and enhanced chemiluminescence (ECL, Amersham).

Reverse Transcriptase-Polymerase Chain Reaction (RT-PCR)

Total RNA from cells was isolated by Trizol reagent (Invitrogen) according to manufacturer's instruction. The RNA was then reverse transcribed using Superscript III (Invitrogen) and the standard PCR procedure was conducted using specific primer sets for p53 and p21 as following; 5'-CCCCTCCTGGCCCCTGTCATCTTC-3' (forward) and 5'-GCAGCGCCTCACAACCTCCGTCAT-3' (reverse) for p53, 5'-GAGGCCGGGATGAGTTGGGAGGAG-3' (forward) and 5'-CAGCCGGCGTTTGGAGTGGTAGAA-3' (reverse) for p21. RT-PCR analysis of GAPDH was used as an internal control for normalization.

Senescence Associated-β-Galactosidase (SA-β-Gal) Staining

Cells in 6-well plates were washed with PBS and fixed with 3% paraformaldehyde. After washing with PBS, the cells were incubated for 24 h at 37° C. (without $CO_2$, protected from light) in freshly prepared SA-β-gal staining solution containing 1 mg/ml 5-bromo-4-chloro-3-indolyl β-D-galactopyranoside (X-gal), 5 mM potassium ferrocyanide, 5 mM potassium ferricyanide, 150 mM NaCl, 2 mM $MgCl_2$ and 40 mM citric acid, titrated with $NaH_2PO_4$ to pH 6.0. SA-β-gal solution was then removed and the cells were washed with PBS. The stained cells were observed under a microscope.

Sirtuin Enzyme Assay

The sirtuin fluorometric assay kits were obtained from Biomol. The assay was conducted according to the manufacturer's instruction. One unit of SirT1 was used per reaction. For SirT2 and SirT3, 2 units were used for the assay. Fluor de Lys substrates and $NAD^+$ were used at 25 μM and 100 μM, respectively.

Endothelial Cell Tube Formation Assay

HUVEC were seeded on a 96-well plate ($2\times10^4$ cells/well) coated with Matrigel. The cells were then incubated for 16~18 h in a humidified 5% $CO_2$ incubator at 37° C. The cells were washed carefully with PBS once and Calcein-AM solution in PBS was then added to a final concentration of 2 μM. After incubation for an additional 30 min, the cells were washed carefully with PBS and observed under a fluorescence microscope (485 nm excitation/520 nm emission). The tube formed was quantified using AngioQuant v1.33 (The MathWorks).

Matrigel Plug Assay In Vivo

Female athymic nude mice (NCR nu/nu, 4-6 weeks old) were purchased from NCI-Frederick, Md. and treated in accordance with Johns Hopkins Animal Care and Use Committee procedures. Control mice were treated with vehicle (5% DMSO in peanut oil) and the test group was treated with 60 mg/kg nitroxoline via i.p. injection. Mice were pre-treated for 3 days before 0.5 mL of Matrigel (BD Biosciences) containing 150 ng/ml VEGF and 200 ng/ml bFGF was implanted subcutaneously. Drug treatment was continued daily for an additional 10 days. Mice were sacrificed, and Matrigel plugs were harvested, fixed in neutral buffered formalin, and processed for histology using MAS-trichrome staining. A cross-section of the entire Matrigel plug was photographed at ×100. And erythrocyte-filled blood vessels were counted per field in a blinded manner.

Breast Cancer Xenografts

Approximately two million of HCC1954 cells were injected bilaterally and subcutaneously into female athymic nude mice (NCR nu/nu, n=5/group). After tumors became palpable, control mice were treated with vehicle (peanut oil with 5% DMSO). The test group was given i.p with 60 mg/kg nitroxoline once daily. The tumor volume was measured using a vernier caliper and calculated according to the modified ellipsoid formula:

Tumor volume $(mm^3)$=(short axis)$^2$×(long axis)×π/6

After 30 days of treatment, the mice were sacrificed and the tumor tissues were extracted for immunohistochemical analysis and Western blots.

Statistical Analysis

Results are expressed as the mean±standard error (SE). Student's t-test was used to determine statistical significance between control and test groups. A P-value of <0.05 was considered statistically significant.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

A number of embodiments of the invention have been described. Embodiments herein include those recited alone or in combination with other delineated embodiments herein. Nevertheless, it will be understood that various modifications may be made without departing from the spirit and scope of the invention. Accordingly, other embodiments are within the scope of the following claims.

What is claimed:

1. A method of treating a disease or disorder associated with methionine aminopeptidase, SirT1, or angiogenesis in a subject, wherein the disease or disorder associated with methionine aminopeptidase, SirT1, or angiogenesis is selected from: tumor or cancer growth (neoplasia), the method comprising the step of administering to the subject an effective amount of nitroxoline;

or a pharmaceutically acceptable salt thereof.

2. The method of claim 1, wherein the subject is identified as being in need of a type 2 methionine aminopeptidase inhibitor.

3. The method of claim 1, wherein the subject is identified as being in need of a SirT1 inhibitor.

4. A method of inhibiting or reducing methionine aminopeptidase or SirT1 in a subject, the method comprising the step of administering to the subject an effective amount of nitroxoline.

5. A method of inhibiting or reducing angiogenesis in a subject, the method comprising the step of administering to the subject an effective amount of nitroxoline;

or a pharmaceutically acceptable salt thereof.

6. A method of treating tumor, cancer growth, or neoplasia in a subject, the method comprising the step of administering to the subject an effective amount of a composition consisting essentially of nitroxoline, or a pharmaceutically acceptable salt thereof.

7. The method of claim 6, wherein the tumor, cancer growth, or neoplasia is selected from the group consisting of ocular cancer, rectal cancer, colon cancer, cervical cancer, prostate cancer, breast cancer, bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

8. The method of claim 1, further comprising administering an additional therapeutic agent to the subject.

9. The method of claim 8, wherein the additional therapeutic agent is an angiogenesis-inhibiting compound.

10. The method of claim 8, wherein the additional therapeutic agent is a methionine aminopeptidase inhibiting compound.

11. The method of claim 8, wherein the additional therapeutic agent is a SirT1 inhibiting compound.

12. The method of claim 8, wherein the additional therapeutic agent is an anticancer compound.

13. The method of claim 1, wherein the step of administering nitroxoline comprises administering the compound orally, topically, parentally, intravenously or intramuscularly.

14. The method of claim 1, wherein the subject is a human.

15. The method of claim 6, wherein the subject is a human.

16. The method of claim 1, wherein the tumor or cancer growth (neoplasia) is selected from the group consisting of ocular cancer, rectal cancer, colon cancer, cervical cancer, prostate cancer, breast cancer, bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

17. The method of claim 16, wherein the tumor or cancer growth (neoplasia) is breast cancer.

18. The method of claim 7, wherein the tumor or cancer growth (neoplasia) is breast cancer.

19. The method of claim 1, wherein the subject is identified as being in need of an angiogenesis inhibitor.

20. The method of claim 6, wherein the tumor, cancer growth, or neoplasia is prostate cancer.

21. The method of claim 6, wherein the tumor, cancer growth, or neoplasia is bladder cancer.

22. The method of claim 6, wherein the tumor, cancer growth, or neoplasia is kidney cancer.

* * * * *